(12) United States Patent
Corcoran et al.

(10) Patent No.: US 8,121,430 B2
(45) Date of Patent: Feb. 21, 2012

(54) DIGITAL IMAGE PROCESSING USING FACE DETECTION AND SKIN TONE INFORMATION

(75) Inventors: Peter Corcoran, Claregalway (IE); Igor Barcovschi, Galway (IE); Eran Steinberg, San Francisco, CA (US); Yury Prilutsky, San Mateo, CA (US); Petronel Bigioi, Galway (IE)

(73) Assignee: DigitalOptics Corporation Europe Limited, Galway (IE)

( * ) Notice: Subject to any disclaimer, the term of this patent is extended or adjusted under 35 U.S.C. 154(b) by 0 days.

(21) Appl. No.: 12/890,185

(22) Filed: Sep. 24, 2010

(65) Prior Publication Data
US 2011/0013043 A1    Jan. 20, 2011

Related U.S. Application Data

(60) Division of application No. 11/554,539, filed on Oct. 30, 2006, now Pat. No. 7,844,076, which is a continuation-in-part of application No. 10/608,810, filed on Jun. 26, 2003, now Pat. No. 7,574,016.

(51) Int. Cl.
*G06K 9/00* (2006.01)
*G06K 9/40* (2006.01)

(52) U.S. Cl. .......... 382/254; 382/118; 382/162

(58) Field of Classification Search .......... 382/100, 382/118, 162–167, 190–195, 254–275, 282–283
See application file for complete search history.

(56) References Cited

U.S. PATENT DOCUMENTS

| | | | | |
|---|---|---|---|---|
| 4,676,753 A | * | 6/1987 | Haggas | 434/155 |
| 5,629,752 A | | 5/1997 | Kinjo | |
| 5,715,377 A | * | 2/1998 | Fukushima et al. | 358/1.9 |
| 5,940,530 A | * | 8/1999 | Fukushima et al. | 382/164 |
| 6,067,399 A | * | 5/2000 | Berger | 386/280 |
| 6,148,092 A | * | 11/2000 | Qian | 382/118 |
| 6,181,805 B1 | | 1/2001 | Koike et al. | |
| 6,275,614 B1 | | 8/2001 | Krishnamurthy et al. | |
| 6,332,033 B1 | * | 12/2001 | Qian | 382/124 |
| 6,351,557 B1 | * | 2/2002 | Gonsalves | 382/167 |
| 6,377,702 B1 | * | 4/2002 | Cooper | 382/167 |
| 6,393,136 B1 | | 5/2002 | Amir et al. | |

(Continued)

FOREIGN PATENT DOCUMENTS
EP    1441497 A2    7/2004
(Continued)

OTHER PUBLICATIONS

Final Office Action mailed Mar. 23, 2010, for U.S. Appl. No. 11/688,236, filed Mar. 19, 2007.

(Continued)

*Primary Examiner* — Manav Seth
(74) *Attorney, Agent, or Firm* — Andrew V. Smith

(57) ABSTRACT

A technique for processing a digital image uses face detection to achieve one or more desired image processing parameters. A group of pixels is identified that corresponds to a face image within the digital image. A skin tone is detected for the face image by determining one or more default color or tonal values, or combinations thereof, for the group of pixels. Values of one or more parameters are adjusted for the group of pixels that correspond to the face image based on the detected skin tone.

21 Claims, 20 Drawing Sheets
(2 of 20 Drawing Sheet(s) Filed in Color)

U.S. PATENT DOCUMENTS

| | | | |
|---|---|---|---|
| 6,504,546 B1 | 1/2003 | Cosatto et al. | |
| 6,816,156 B2 | 11/2004 | Sukeno et al. | |
| 6,847,373 B1 * | 1/2005 | Gonsalves et al. | 345/589 |
| 6,954,549 B2 * | 10/2005 | Kraft | 382/167 |
| 6,975,759 B2 * | 12/2005 | Lin | 382/167 |
| 7,012,617 B2 * | 3/2006 | Luo et al. | 345/593 |
| 7,024,053 B2 | 4/2006 | Enomoto | |
| 7,039,222 B2 * | 5/2006 | Simon et al. | 382/118 |
| 7,184,578 B2 * | 2/2007 | Simon et al. | 382/118 |
| 7,187,788 B2 * | 3/2007 | Simon et al. | 382/118 |
| 7,212,657 B2 * | 5/2007 | Simon et al. | 382/118 |
| 7,321,391 B2 | 1/2008 | Ishige | |
| 7,352,393 B2 | 4/2008 | Sakamoto | |
| 7,502,494 B2 | 3/2009 | Tafuku et al. | |
| 7,551,211 B2 | 6/2009 | Taguchi et al. | |
| 7,573,505 B2 * | 8/2009 | Kawaguchi et al. | 348/222.1 |
| 7,602,949 B2 * | 10/2009 | Simon et al. | 382/118 |
| 7,612,794 B2 | 11/2009 | He et al. | |
| 7,623,733 B2 | 11/2009 | Hirosawa | |
| 7,636,485 B2 | 12/2009 | Simon et al. | |
| 7,652,693 B2 | 1/2010 | Miyashita et al. | |
| 7,733,388 B2 | 6/2010 | Asaeda | |
| 2002/0081003 A1 | 6/2002 | Sobol | |
| 2002/0150291 A1 | 10/2002 | Naf et al. | |
| 2003/0117501 A1 | 6/2003 | Shirakawa | |
| 2005/0036044 A1 | 2/2005 | Funakura | |
| 2006/0153470 A1 * | 7/2006 | Simon et al. | 382/254 |
| 2006/0204034 A1 | 9/2006 | Steinberg et al. | |
| 2006/0228037 A1 | 10/2006 | Simon et al. | |
| 2007/0160307 A1 | 7/2007 | Steinberg et al. | |
| 2008/0013799 A1 | 1/2008 | Steinberg et al. | |
| 2008/0143854 A1 | 6/2008 | Steinberg et al. | |
| 2008/0175481 A1 | 7/2008 | Petrescu et al. | |
| 2009/0052749 A1 | 2/2009 | Steinberg et al. | |
| 2009/0052750 A1 | 2/2009 | Steinberg et al. | |
| 2009/0087042 A1 | 4/2009 | Steinberg et al. | |
| 2009/0175609 A1 | 7/2009 | Tan | |
| 2009/0244296 A1 | 10/2009 | Petrescu et al. | |
| 2009/0245693 A1 | 10/2009 | Steinberg et al. | |

FOREIGN PATENT DOCUMENTS

| | | |
|---|---|---|
| EP | 1453002 A2 | 9/2004 |
| WO | WO 00/76398 A1 | 12/2000 |
| WO | WO 2007/128117 A1 | 11/2007 |
| WO | WO 2010/012448 A2 | 2/2010 |
| WO | WO 2010/012448 A3 | 6/2010 |

OTHER PUBLICATIONS

Machin, et al., Real Time Facial Motion Analysis for Virtual Teleconferencing, IEEE, 1996, pp. 340-344.

Ming, et al., Human Face Orientation Estimation Using Symmetry and Feature Points Analysis, IEEE, 2000, pp. 1419-1422.

Non-Final Office Action mailed Apr. 2, 2010, for U.S. Appl. No. 10/608,784, filed Jun 26, 2003.

Non-Final Office Action mailed Apr. 30, 2010, for U.S. Appl. No. 11/765,899, filed Jun. 20, 2007.

PCT Notification of Transmittal of the International Search Report and the Written Opinion of the International Searching Authority, or the Declaration, for PCT Application No. PCT/EP2009/005461, dated Apr. 20, 2010, 12 pages.

Yao, Christina, Image Cosmetics: An automatic Skin Exfoliation Framework on Static Images, UCSB Four Eyes Lab Imaging, Interaction, and Innovative Interfaces Publications Thesis, Master of Science in Media Arts and Technology Dec. 2005, pp. 1-83, Retrieved from the Internet : URL: http://ilab.cs.ucsb.edu/publications/YaoMS.pdf.

Co-pending U.S. Appl. No. 12/790,594, filed May 28, 2010.

Co-pending U.S. Appl. No. 12/825,280, filed Jun. 28, 2010.

Co-pending U.S. Appl. No. 12/843,805, filed Jul. 26, 2010.

Final Office Action mailed Sep. 1, 2010, for U.S. Appl. No. 10/608,784, filed Jun. 26, 2003.

Non-Final Office Action mailed Aug. 2, 2010, for U.S. Appl. No. 11/688,236, filed Mar. 19, 2007.

Non-Final Office Action mailed Jun. 14, 2010, for U.S. Appl. No. 11/624,683, filed Jan. 18, 2007.

Non-Final Office Action mailed Jun. 16, 2010, for U.S. Appl. No. 12/482,305, filed Jun. 10, 2009.

Non-Final Office Action mailed Jun. 22, 2010, for U.S. Appl. No. 12/055,958, filed Mar. 26, 2008.

Non-Final Office Action mailed Jun. 23, 2010, for U.S. Appl. No. 11/941,956, filed Nov. 18, 2007.

Notice of Allowance mailed Aug. 23, 2010, for U.S. Appl. No. 12/262,024, filed Oct. 30, 2008.

Notice of Allowance mailed Jun. 10, 2010, for U.S. Appl. No. 12/262,024, filed Oct. 30, 2008.

Notice of Allowance mailed Sep. 2, 2010, for U.S. Appl. No. 12/262,071, filed Oct. 30, 2008.

Notice of Allowance mailed Sep. 3, 2010, for U.S. Appl. No. 12/262,061, filed Oct. 30, 2008.

* cited by examiner

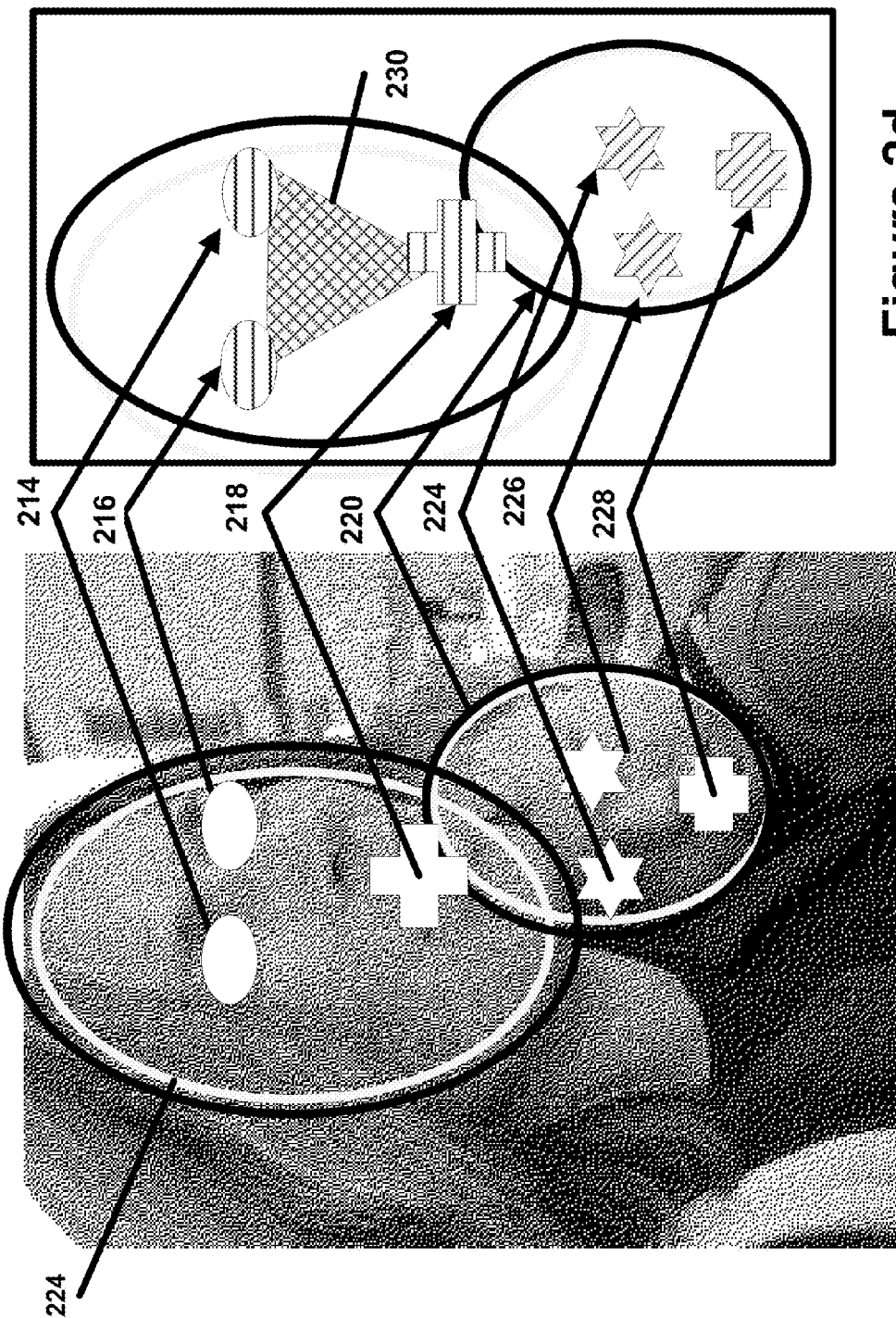

The original image (a dark background)

After local dark face "correction"

The original image (a light background)

After "correction"

ial Ratio", also known as the "divine proportion" in the Renaissance period, or PHI, φ-lines. Some
DIGITAL IMAGE PROCESSING USING FACE DETECTION AND SKIN TONE INFORMATION

CROSS-REFERENCE TO RELATED APPLICATIONS

This application is a Division of U.S. patent application Ser. No. 11/554,539, filed Oct. 30, 2006, now U.S. Pat. No. 7,844,076; which is a continuation-in-part (CIP) of U.S. patent application Ser. No. 10/608,810, filed Jun. 26, 2003, now U.S. Pat. No. 7,574,016; including U.S. application Ser. No. 10/608,887, now U.S. Pat. No. 7,616,233; U.S. application Ser. No. 10/608,888, now U.S. Pat. No. 7,362,368; U.S. application Ser. No. 10/608,811, now U.S. Pat. No. 7,471,846; U.S. application Ser. No. 10/608,772, now U.S. Pat. No. 7,440,593; U.S. application Ser. No. 10/608,784, published as US2006/0204034; U.S. application Ser. No. 10/608,766, now U.S. Pat. No. 7,317,815; U.S. application Ser. No. 10/608,919, now U.S. Pat. No. 7,269,292; Ser. No. 10/608,824, now U.S. Pat. No. 7,315,630; and is related as well to U.S. application Ser. No. 11/024,046, now U.S. Pat. No. 7,565,030; and PCT/US2006/021393, published as WO 2007/142621, which are hereby incorporated by reference.

BACKGROUND OF THE INVENTION

1. Field of the Invention

The invention relates to digital image processing, particularly automatic suggesting or processing of enhancements of a digital image using information gained from identifying and analyzing faces appearing within the image, and detecting a skin tone of the faces. The invention provides automated image processing methods and tools for photographs taken and/or images detected, acquired or captured in digital form or converted to digital form, or rendered from digital form to a soft or hard copy medium by using information about the faces in the photographs and/or images, and particularly for adjusting a fill-flash based on the detected skin tone of each face.

2. Description of the Related Art

The problem of face detection has not received a great deal of attention from researchers. Most conventional techniques concentrate on face recognition, assuming that a region of an image containing a single face has already been extracted and will be provided as an input. Such techniques are unable to detect faces against complex backgrounds or when there are multiple occurrences in an image. For all of the image enhancement techniques introduced below and others as may be described herein or understood by those skilled in the art, it is desired to make use of the data obtained from face detection processes for suggesting options for improving digital images or for automatically improving or enhancing quality of digital images.

Yang et al., IEEE Transactions on Pattern Analysis and Machine Intelligence, Vol. 24, No. 1, pages 34-58, give a useful and comprehensive review of face detection techniques January 2002. These authors discuss various methods of face detection which may be divided into four main categories: (i) knowledge-based methods; (ii) feature-invariant approaches, including the identification of facial features, texture and skin color; (iii) template matching methods, both fixed and deformable and (iv) appearance based methods, including eigenface techniques, statistical distribution based methods and neural network approaches. They also discuss a number of the main applications for face detections technology. It is recognized in the present invention that none of this prior art describes or suggests using detection and knowledge of faces in images to create and/or use tools for the enhancement or correction of the images.

a. Faces as Subject Matter

Human faces may well be by far the most photographed subject matter for the amateur and professional photographer. In addition, the human visual system is very sensitive to faces in terms of skin tone colors. Also, in experiments performed by tracking the eye movement of the subjects, with an image that includes a human being, subjects tend to focus first and foremost on the face and in particular the eyes, and only later search the image around the figure. By default, when a picture includes a human figure and in particular a face, the face becomes the main object of the image. Thus, many artists and art teachers emphasize the location of the human figure and the face in particular to be an important part of a pleasing composition. For example, some teach to position faces around the "Golden Ratio", also known as the "divine proportion" in the Renaissance period, or PHI, φ-lines. Some famous artists whose work repeatedly depict this composition are Leonardo Da-Vinci, Georges Seurat and Salvador Dali.

In addition, the faces themselves, not just the location of the faces in an image, have similar "divine proportion" characteristics. The head forms a golden rectangle with the eyes at its midpoint; the mouth and nose are each placed at golden sections of distance between the eyes and the bottom on the chin etc. etc.

b. Color and Exposure of Faces

While the human visual system is tolerant to shifts in color balance, the human skin tone is one area where the tolerance is somewhat limited and is accepted primarily only around the luminance axis, which is a main varying factor between skin tones of faces of people of different races or ethnic backgrounds. A knowledge of faces can provide an important advantage in methods of suggesting or automatically correcting an overall color balance of an image, as well as providing pleasing images after correction.

c. Auto Focus

Auto focusing is a popular feature among professional and amateur photographers alike. There are various ways to determine a region of focus. Some cameras use a center-weighted approach, while others allow the user to manually select the region. In most cases, it is the intention of the photographer to focus on the faces photographed, regardless of their location in the image. Other more sophisticated techniques include an attempt to guess the important regions of the image by determining the exact location where the photographer's eye is looking It is desired to provide advantageous auto focus techniques which can focus on what is considered the important subject in the image d. Fill-Flash Another useful feature particularly for the amateur photographer is fill-flash mode. In this mode, objects close to the camera may receive a boost in their exposure using artificial light such as a flash, while far away objects which are not effected by the flash are exposed using available light. It is desired to have an advantageous technique which automatically provides image enhancements or suggested options using fill flash to add light to faces in the foreground which are in the shadow or shot with back light.

e. Orientation

The camera can be held horizontally or vertically when the picture is taken, creating what is referred to as a landscape mode or portrait mode, respectively. When viewing images, it is preferable to determine ahead of time the orientation of the camera at acquisition, thus eliminating a step of rotating the image and automatically orienting the image. The system may try to determine if the image was shot horizontally, which is also referred to as landscape format, where the width is larger than the height of an image, or vertically, also referred to as portrait mode, where the height of the image is larger than the width. Techniques may be used to determine an orientation of an image. Primarily these techniques include either recording the camera orientation at an acquisition time using an in camera mechanical indicator or attempting to analyze image content post-acquisition. In-camera methods, although providing precision, use additional hardware and sometimes movable hardware components which can increase the price of the camera and add a potential maintenance challenge. However, post-acquisition analysis may not generally provide sufficient precision. Knowledge of location, size and orientation of faces in a photograph, a computerized system can offer powerful automatic tools to enhance and correct such images or to provide options for enhancing and correcting images.

f. Color Correction

Automatic color correction can involve adding or removing a color cast to or from an image. Such cast can be created for many reasons including the film or CCD being calibrated to one light source, such as daylight, while the lighting condition at the time of image detection may be different, for example, cool-white fluorescent. In this example, an image can tend to have a greenish cast that it will be desired to be removed. It is desired to have automatically generated or suggested color correction techniques for use with digital image enhancement processing.

g. Cropping

Automatic cropping may be performed on an image to create a more pleasing composition of an image. It is desired to have automatic image processing techniques for generating or suggesting more balanced image compositions using cropping.

h. Rendering

When an image is being rendered for printing or display, it undergoes operation as color conversion, contrast enhancement, cropping and/or resizing to accommodate the physical characteristics of the rendering device. Such characteristic may be a limited color gamut, a restricted aspect ratio, a restricted display orientation, fixed contrast ratio, etc. It is desired to have automatic image processing techniques for improving the rendering of images.

i. Compression and Resolution

An image can be locally compressed in accordance with a preferred embodiment herein, so that specific regions may have a higher quality compression which involves a lower compression rate. It is desired to have an advantageous technique for determining and/or selecting regions of importance that may be maintained with low compression or high resolution compared with regions determined and/or selected to have less importance in the image.

SUMMARY OF THE INVENTION

A method of processing a digital image using face detection is provided to achieve one or more desired image processing parameters. A group of pixels is identified that corresponds to a face image within the digital image. A skin tone for the face image is detected by determining one or more default color or tonal values, or combinations thereof, for the group of pixels. Values of one or more parameters for the group of pixels that correspond to the face image are adjusted based on the detected skin tone.

The adjusting may include applying fill-flash or adjusting a luminance to the face image in an amount depending on the skin tone.

The identifying, detecting and adjusting may be repeated for a second face image having a different skin tone than the first face image. The adjusting may then include applying fill-flash to or adjusting luminance of the two face images in different relative amounts depending on the different skin tones.

The color or tonal values for the group of pixels may include one or more average color or tonal values, and may include multiple colors or tones, or combinations thereof, determined for each of multiple regions of the face image.

A further method of processing a digital image using face detection is provided to achieve one or more desired image processing parameters. A group of pixels is identified that corresponds to a face image within the digital image. A luminance of the face image is detected by determining one or more default luminance values for the group of pixels. A fill-flash is provided for the face image based on the detected luminance.

A second group of pixels may be identified that corresponds to a second face within the digital image. The luminance of the second face image, which differs from that of the first face image, may be detected. Fill-flash is provided for the second face image which differs from that provided for the first face image. The corrected luminances of the two face images may be preferably closer to each other than their original luminances, they may be substantially equal to each other.

A skin tone may be detected for the face image by determining one or more default color or tonal values, or combinations thereof, for the group of pixels. Values may be adjusted of one or more parameters for the group of pixels that correspond to the face image based on the detected skin tone.

Each of the methods provided are preferably implemented within software and/or firmware either in an imaging capture device such as a digital still or video camera or with external processing equipment. The software may also be downloaded into the camera or image processing equipment. In this sense, one or more processor readable storage devices having processor readable code embodied thereon are provided. The processor readable code programs one or more processors to perform any of the above or below described methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2a-2e illustrate image orientation based on orientation of faces in accordance with one or more preferred embodiments.

INCORPORATION BY REFERENCE

Figure 1A:
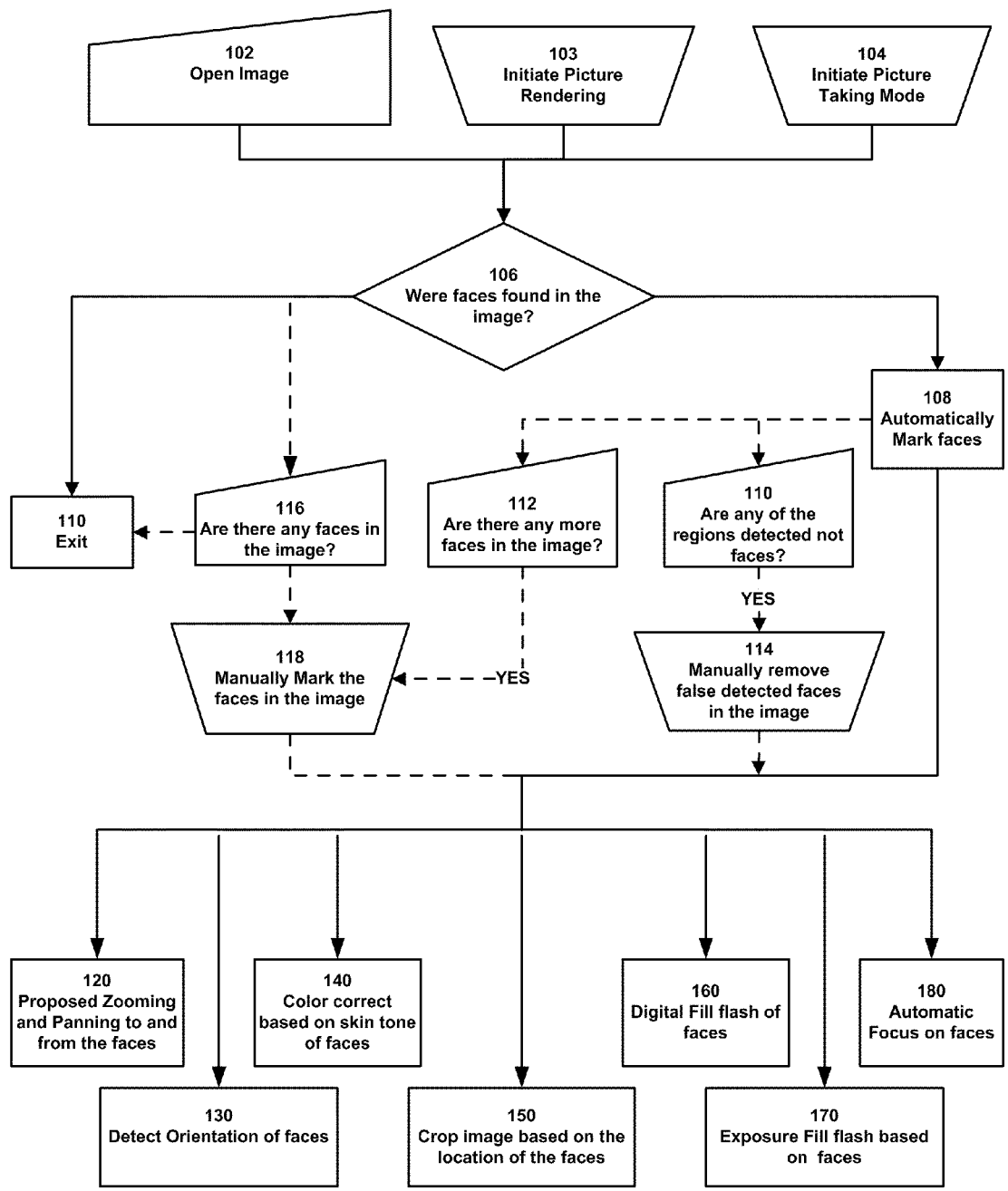
FIG. 1a illustrates a preferred embodiment of the main workflow of correcting images based on finding faces in the images.

What follows is a cite list of references each of which is, in addition to that which is described as background, the invention summary, the abstract, the brief description of the drawings and the drawings themselves, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description herein:

U.S. Pat. Nos. RE33682, RE31370, 4,047,187, 4,317,991, 4,367,027, 4,638,364, 5,291,234, 5,488,429, 5,638,136, 5,710,833, 5,724,456, 5,781,650, 5,812,193, 5,818,975, 5,835,616, 5,870,138, 5,978,519, 5,991,456, 6,097,470, 6,101,271, 6,128,397, 6,148,092, 6,151,073, 6,188,777, 6,192,149, 6,249,315, 6,263,113, 6,268,939, 6,282,317, 6,301,370, 6,332,033, 6,393,148, 6,404,900, 6,407,777, 6,421,468, 6,438,264, 6,456,732, 6,459,436, 6,473,199, 6,501,857, 6,504,942, 6,504,951, 6,516,154, and 6,526,161;

United States published patent applications no. 2003/0071908, 2003/0052991, 2003/0025812, 2002/0172419, 2002/0114535, 2002/0105662, and 2001/0031142;

Japanese patent application no. JP5260360A2;

British patent application no. GB0031423.7; and

Yang et al., IEEE Transactions on Pattern Analysis and Machine Intelligence, Vol. 24, no. 1, pp 34-58 (January 2002); and Baluja & Rowley, "Neural Network-Based Face Detection," IEEE Transactions on Pattern Analysis and Machine Intelligence, Vol. 20, No. 1, pages 23-28, January 1998.

ILLUSTRATIVE DEFINITIONS

"Face Detection" involves the art of isolating and detecting faces in a digital image; Face Detection includes a process of determining whether a human face is present in an input image, and may include or is preferably used in combination with determining a position and/or other features, properties, parameters or values of parameters of the face within the input image;

"Image-enhancement" or "image correction" involves the art of modifying a digital image to improve its quality; such modifications may be "global" applied to the entire image, or "selective" when applied differently to different portions of the image. Some main categories non-exhaustively include:
  (i) Contrast Normalization and Image Sharpening.
  (ii) Image Crop, Zoom and Rotate.
  (iii) Image Color Adjustment and Tone Scaling.
  (iv) Exposure Adjustment and Digital Fill Flash applied to a Digital Image.
  (v) Brightness Adjustment with Color Space Matching; and Auto-Gamma determination with Image Enhancement.
  (vi) Input/Output device characterizations to determine Automatic/Batch Image Enhancements.
  (vii) In-Camera Image Enhancement
  (viii) Face Based Image Enhancement "Auto-focusing" involves the ability to automatically detect and bring a photographed object into the focus field;

"Fill Flash" involves a method of combining available light, such as sun light with another light source such as a camera flash unit in such a manner that the objects close to the camera, which may be in the shadow, will get additional exposure using the flash unit.

A "pixel" is a picture element or a basic unit of the composition of a digital image or any of the small discrete elements that together constitute an image;

"Digitally-Captured Image" includes an image that is digitally located and held in a detector;

"Digitally-Acquired Image" includes an image that is digitally recorded in a permanent file and/or preserved in a more or less permanent digital form, e.g., for later retrieval;

"Digitally-Detected Image": an image comprising digitally detected electromagnetic waves; and "Digital Rendering Device": A digital device that renders digital encoded information such as pixels onto a different device. Most common rendering techniques include the conversion of digital data into hard copy such as printers, and in particular laser printers, ink jet printers or thermal printers, or soft copy devices such as monitors, television, liquid crystal display, LEDs, OLED, etc.

DETAILED DESCRIPTION OF THE PREFERRED EMBODIMENTS

Preferred embodiments are described below including methods and devices for providing or suggesting options for automatic digital image enhancements based on information relating to the location, position, focus, exposure or other parameter or values of parameters of faces in an image. Such parameters or values of parameter may include a spatial parameter. For example, an orientation of a face or faces within an digital image may be used to adjust or suggest an adjustment of an orientation of the entire image or of one or more faces within the image. Color correction or enhancement may be automatically suggested or provided for digital images based on color or tonal values of faces in the image. Pleasing cropping of images may be suggested or provided based on knowledge particularly of the location and/or size of faces in the image.

A still image may be animated and used in a slide show by, e.g., zooming, panning and/or rotating where the center point of an image is within a face or at least the face is included in all or substantially all of the images in the slide show. Selective compression, or alternatively selective resolution, or both, of images may be suggested or automatically provided where one or more faces receive higher grade compression and/or alternatively higher local resolution than other portions of the image. A fill flash may be automatically digitally simulated or suggested, or actually applied to an object, upon analysis of a luminance map of the image. A camera may also be automatically focused prior to acquiring an image based on knowledge regarding the faces in an image.

A preferred embodiment includes an image processing application whether implemented in software or in firmware, as part of the image capture process, image rendering process, or as part of post processing. This system receives images in digital form, where the images can be translated into a grid representation including multiple pixels. This application detects and isolates the faces from the rest of the picture, and determines sizes and locations of the faces relative to other portions of the image or the entire image. Orientations of the faces may also be determined. Based on information regarding detected faces, preferably separate modules of the system collect facial data and perform image enhancement operations based on the collected facial data. Such enhancements or corrections include automatic orientation of the image, color correction and enhancement, digital fill flash simulation and dynamic compression.

In another embodiment, the information regarding the location and size of faces in an image assist in determining correct auto focus distance and exposure in the camera. In a separate embodiment, such information can be processed in the camera as part of the post processing stage such that the saved image is already automatically corrected, enhanced and/or adjusted based on this information.

Advantages of the preferred embodiments include the ability to automatically perform or suggest or assist in performing complex tasks that may otherwise call for manual intervention and/or experimenting. Another advantage is that important regions, e.g., faces, of an image may be assigned, marked and/or mapped and then processing may be automatically performed and/or suggested based on this information relating to important regions of the images. Automatic assistance may be provided to a photographer in the post processing stage. Assistance may be provided to the photographer in determining a focus and an exposure while taking a picture. Meta-data may be generated in the camera that would allow an image to be enhanced based on the face information.

Many advantageous techniques are provided in accordance with preferred and alternative embodiments set forth herein. For example, a method of processing a digital image using face detection within said image to achieve one or more desired image processing parameters is provided. A group of pixels is identified that correspond to an image of a face within the digital image. Default values are determined of one or more parameters of at least some portion of said digital image. Values of the one or more parameters are adjusted within the digitally-detected image based upon an analysis of said digital image including said image of said face and said default values.

The digital image may be digitally-acquired and/or may be digitally-captured. Decisions for processing the digital image based on said face detection, selecting one or more parameters and/or for adjusting values of one or more parameters within the digital image may be automatically, semi-automatically or manually performed. Similarly, on the other end of the image processing workflow, the digital image may be rendered from its binary display onto a print, or a electronic display.

The one or more parameter may include orientation, color, tone, size, luminance, relative exposure, relative spatial location, tone reproduction, sharpness or focus or combinations thereof. The one or more parameters may include a mask that defines one or more regions where the one or more parameters are valid. The mask may include a continuous presentation of varying strength within different sub-regions of said one or more regions. The one or more parameters may include the same parameter differing in value based on said mask.

Two or more parameters may be concatenated into a single parameter. The digital image may be transformed based on values of the one or more parameters. An operation list may be created for the digital image based on values of the one or more parameters. The operation list may be embedded within the digital image or may be external to the digital image.

Values of orientation may be adjusted such that a rotation value for the digital image is determined. Values of the color, tone, size, luminance, relative exposure may be adjusted including manipulating a color, tonal, size, luminance, fill-flash balance of the digital image, respectively. Values of relative spatial location may be adjusted including adjusting a spatial location of an image of a face relative to at least one other region of the digital image. Values of focus may be adjusted including adjusting values of focus for enhancing a focus of the image of the face within the digital image.

One or more different degrees of simulated fill flash may be created by manual, semi-automatic or automatic adjustment. The analysis of the image of the face may include a comparison of an overall exposure to an exposure around the identified face. The exposure may be calculated based on a histogram. Digitally simulation of a fill flash may include optionally adjusting tone reproduction and/or locally adjusting sharpness. One or more objects estimated to be closer to the camera or of higher importance may be operated on in the simulated fill-flash. These objects determined to be closer to the camera or of higher importance may include one or more identified faces. A fill flash or an option for providing a suggested fill-flash may be automatically provided. The method may be performed within a digital acquisition device, a digital rendering device, or an external device or a combination thereof.

The face pixels may be identified, a false indication of another face within the image may be removed, and an indication of a face may be added within the image, each manually by a user, or semi-automatically or automatically using image processing apparatus. The face pixels identifying may be automatically performed by an image processing apparatus, and a manual verification of a correct detection of at least one face within the image may be provided.

A method of digital image processing using face detection to achieve a desired image parameter is further provided including identifying a group of pixels that correspond to an image of a face within a digitally-detected image. Initial values of one or more parameters of at least some of the pixels are determined. An initial parameter of the digitally-detected image is determined based on the initial values. Values of the one or more parameters of pixels within the digitally-detected image are automatically adjusted based upon a comparison of the initial parameter with the desired parameter or an option for adjusting the values is automatically provided.

The digitally-detected image may include a digitally-acquired, rendered and/or digitally-captured image. The initial parameter of the digitally-detected image may include an initial parameter of the face image. The one or more parameters may include any of orientation, color, tone, size, luminance, and focus. The method may be performed within a digital camera as part of a pre-acquisition stage, within a camera as part of post processing of the captured image or within external processing equipment. The method may be performed within a digital rendering device such as a printer, or as a preparation for sending an image to an output device, such as in the print driver, which may be located in the printer or on an external device such as the PC, as part of a preparation stage prior to displaying or printing the image. An option to manually remove a false indication of a face or to add an indication of a face within the image may be included. An option to manually override, the automated suggestion of the system, whether or not faces were detected, may be included.

The method may include identifying one or more subgroups of pixels that correspond to one or more facial features of the face. Initial values of one or more parameters of pixels of the one or more sub-groups of pixels may be determined. An initial spatial parameter of the face within the digital image may be determined based on the initial values. The initial spatial parameter may include any of orientation, size and location.

When the spatial parameter is orientation, values of one or more parameters of pixels may be adjusted for re-orienting the image to an adjusted orientation. The one or more facial features may include one or more of an eye, a mouth, two eyes, a nose, an ear, neck, shoulders and/or other facial or personal features, or other features associated with a person such as an article of clothing, furniture, transportation, outdoor environment (e.g., horizon, trees, water, etc.) or indoor environment (doorways, hallways, ceilings, floors, walls, etc.), wherein such features may be indicative of an orientation. The one or more facial or other features may include two or more features, and the initial orientation may be determined base on relative positions of the features that are determined based on the initial values. A shape such as a triangle may be generated for example between the two eyes and the center of the mouth, a golden rectangle as described above, or more generically, a polygon having points corresponding to preferably three or more features as vertices or axis.

Initial values of one or more chromatic parameters, such as color and tone, of pixels of the digital image may be determined. The values of one or more parameters may be automatically adjusted or an option to adjust the values to suggested values may be provided.

Within a digital acquisition device, a method of perfecting acquisition parameters of a digital image as part of an image capture process using face detection within said captured image to achieve one or more desired image acquisition parameters is provided. Default values are determined of one or more image attributes of at least some portion of the digital image. Values of one or more camera acquisition parameters are determined. Groups of pixels are identified that correspond to an image of a face within the digitally-captured image. Corresponding image attributes to the groups of pixels are determined. One or more default image attribute values are compared with one or more captured image attribute values based upon analysis of the image of the face. Camera acquisition parameters are then adjusted corresponding to adjusting the image attribute values.

The method may be performed within any digital image capture device, which as, but not limited to digital still camera or digital video camera. The one or more parameters may include overall exposure, relative exposure, orientation, color balance, white point, tone reproduction, size, or focus, or combinations thereof. The face pixels identifying may be automatically performed by an image processing apparatus, and the method may include manually removing one or more of the groups of pixels that correspond to an image of a face. An automatically detected face may be removed in response to false detection of regions as faces, or in response to a determination to concentrate on less image faces or images faces that were manually determined to be of higher subjective significance, than faces identified in the identifying step. A face may be removed by increasing a sensitivity level of said face identifying step. The face removal may be performed by an interactive visual method, and may use an image acquisition built-in display.

The face pixels identifying may be performed with an image processing apparatus, and may include manually adding an indication of another face within the image. The image processing apparatus may receive a relative value as to a detection assurance or an estimated importance of the detected regions. The relative value may be manually modified as to the estimated importance of the detected regions.

Within a digital camera, a method of digital image processing using face detection for achieving a desired image parameter is further provided. A group of pixels is identified that correspond to a face within a digital image. First initial values of a parameter of pixels of the group of pixels are determined, and second initial values of a parameter of pixels other than pixels of the group of pixels are also determined. The first and second initial values are compared. Adjusted values of the parameter are determined based on the comparing of the first and second initial values and on a comparison of the parameter corresponding to at least one of the first and second initial values and the desired image parameter.

Initial values of luminance of pixels of the group of pixels corresponding to the face may be determined. Other initial values of luminance of pixels other than the pixels corresponding to the face may also be determined. The values may then be compared, and properties of aperture, shutter, sensitivity and a fill flash may be determined for providing adjusted values corresponding to at least some of the initial values for generating an adjusted digital image. The pixels corresponding to the face may be determined according to sub-groups corresponding to one or more facial features.

Within a digital acquisition device with an adjustable optical system having an auto focusing mechanism, a method of perfecting the auto focus mechanism of the adjustable optical system as part of an image capture process using face detection in the image capture process to achieve one or more desired image acquisition parameters is provided. Groups of pixels are identified that correspond to an image of a face within a digitally-captured image. Corresponding image attributes to the groups of pixels are determined. Auto focus is perfected by performing the auto focus on the plural groups of pixels that correspond to the image of the face.

The auto focus may be initially performed on the entire image. The method for auto-focusing the lens and the automatic adjusting automatically adjusting one or more properties of the adjustable optical system. A user may manually activate the camera to perform the perfecting of the auto focus. The face pixels identifying may be automatically performed by an image processing apparatus, and one or more of the groups of pixels detected as faces may be manually removed in response to false detection of one or more regions as one or more faces, or in response to a determination to concentrate on less image faces than faces identified in the identifying step. The faces may be removed by increasing a sensitivity level of the face identifying step and/or by an interactive visual method. An image acquisition built-in display may be used. A weighted average on individual objects of the groups may be used in the auto-focus process. The face identifying step may be automatically performed by an image processing apparatus which receives a relative value as to detection assurance. In this case, a weighted average may be calculated based on the relative values as to the detection assurance. The face pixels identifying may be automatically performed by an image processing apparatus which receives a relative value as to an estimated importance of the detected regions. In this case, A weighted average may be calculated based on the relative values as to the estimated detection assurance. The estimated importance of the detected regions of faces may involve an analysis of a parameter such as size of the faces, location of the faces within the captured image, or relative exposure of the faces, or combinations thereof.

Within a digital camera having a lens system, a method of adjusting the capture parameters of a digitally-detected image based on detection of faces within the image to achieve a desired image parameter is also provided. The method may be used for auto-focusing the lens as part of the acquisition process. One or more parameters of pixels of the face image are determined. Values of the one or more parameters of the pixels may be automatically adjusted based upon a comparison of the initial parameter with the desired parameter. For example, one or more properties of the lens system may be automatically adjusted based on the values to adjust the focus, an indication to the region of focus or an adjustment option may be provided. The one or more parameters may include a spatial parameter such as a size and/or a location of the face in the image.

Within a digital acquisition device with a built in flash unit, a method of perfecting the exposure of an acquired digital image using face detection in the acquired image is provided. Groups of pixels that correspond to plural images of faces are identified within a digitally acquired image, and corresponding image attributes to the group of pixels are determined. An analysis is performed of the corresponding attributes of the groups of pixels. It is then determined to activate the built-in flash unit based on the analysis. An intensity of the built-in flash unit is determined based on the analysis.

An initial step of calculating image attributes may be performed on an entire acquired digital image and image attributes may be compared to the image attributes of the group of pixels. The image attributes may include exposure. The exposure may be calculated as a function of one or more parameters including aperture, speed, gain, or relative sensitivity, or combinations thereof. The groups of pixels of faces may be given a certain weight based on weight criteria. The weight criteria may be calculated based on a distance of the groups of pixels to the camera. The weight criteria may be calculated based on relative sizes of the groups of pixels.

A pre-flash may be performed based on the calculated flash intensity to determine whether the analysis is accurate. A second analysis may be performed based on the pre-flash.

One or more different degrees of simulated fill flash may be created by manual, semi-automatic or automatic adjustment. The analysis of the image of the face may include a comparison of an overall exposure to an exposure around the identified face. The exposure may be calculated based on a histogram. Digitally simulation of a fill flash may include optionally adjusting tone reproduction and/or locally adjusting sharpness. One or more objects estimated to be closer to the camera or of higher importance may be operated on in the simulated fill-flash. These objects determined to be closer to the camera or of higher importance may include one or more identified faces. A fill flash or an option for providing a suggested fill-flash may be automatically provided.

Within a digital camera, a further method of digital image processing using face detection for achieving a desired image parameter is provided. A group of pixels is identified that correspond to a face within a digital image. First initial values are determined of a parameter of pixels of the group of pixels. Second initial values of a parameter are determined of pixels other than pixels of the group of pixels. The first and second initial values are compared. Adjusted values of the parameter are determined based on the comparing of the first and second initial values and on a comparison of the parameter corresponding to at least one of the first and second initial values and the desired image parameter.

The parameter may include luminance, and the method may further include automatically generating the adjusted digital image using the adjusted values. The method may also further include automatically providing an option to generate the adjusted digital image using the adjusted values. The adjusted values of the luminance may be provided by a fill flash, or by a digitally-simulated fill flash.

Within a digital camera, a further method of digital image processing using face detection to achieve a desired luminance contrast is provided. A group of pixels is identified that correspond to a face within a digital image. First initial values of luminance of pixels of the group of pixels are determined. Second initial values of luminance of pixels other than pixels of the group of pixels are also determined. The first and second initial values are compared to determine an initial luminance contrast. Properties of a fill flash are determined for providing adjusted values of luminance for at least some of the pixels of the digital image based on a comparison of the initial luminance contrast and the desired luminance contrast.

Within a digital rendering device, a further method of digital image processing using face detection for achieving a desired image rendering parameters is provided. A group of pixels is identified that correspond to a face within a digital image. First initial values are determined of a parameter of pixels of the group of pixels. Second initial values of a parameter are determined of pixels other than pixels of the group of pixels. The first and second initial values are compared. Adjusted values of the parameter are determined based on the comparing of the first and second initial values and on a comparison of the rendering parameter corresponding to at least one of the first and second initial values and the desired image rendering parameter.

The parameter may include luminance, and the method may further include automatically generating the adjusted digital image using the adjusted values. The method may also further include automatically providing an option to generate the adjusted digital image using the adjusted values. The adjusted values of the luminance may be provided by changing the ink coverage, the display luminance values, etc.

Within a digital rendering device, a further method of digital image processing using face detection to achieve a desired contrast and color balance is provided. A group of pixels is identified that correspond to a face within a digital image. First initial values of contrast and/or color balance of pixels of the group of pixels are determined. Second initial values of contrast and/or color balance of pixels other than pixels of the group of pixels are also determined. The first and second initial values are compared to determine an initial contrast and/or color balance. Such tool may compensate for the disparity between the input or digitally acquired image and the output device. Such discrepancies may arise due to a mismatching of color gamut, the physical characteristic of the display, reflective or self luminance the limited contrast, the effect of the surrounding environment, etc.

A method of generating one or more new digital images using an original digitally-acquired image including a face is further provided. A group of pixels that correspond to a face within the original digitally-acquired image is identified. A portion of the original image is selected to include the group of pixels. Values of pixels of one or more new images based on the selected portion are automatically generated, or an option to generate them is provided, in a manner which always includes the face within the one or more new images.

A transformation may be gradually displayed between the original digitally-acquired image and one or more new images. Parameters of said transformation may be adjusted between the original digitally-acquired image and one or more new images. Parameters of the transformation between the original digitally-acquired image and one or more new images may be selected from a set of at least one or more criteria including timing or blending or a combination thereof. The blending may include dissolving, flying, swirling, appearing, flashing, or screening, or combinations thereof.

Methods of generating slide shows that use an image including a face are provided in accordance with the generation of one or more new images. A group of pixels is identified that correspond to a face within a digitally-acquired image. A zoom portion of the image including the group of pixels may be determined. The image may be automatically zoomed to generate a zoomed image including the face enlarged by the zooming, or an option to generate the zoomed image may be provided. A center point of zooming in or out and an amount of zooming in or out may be determined after which another image may be automatically generated including a zoomed version of the face, or an option to generate the image including the zoomed version of the face may be provided. One or more new images may be generated each including a new group of pixels corresponding to the face, automatic panning may be provided using the one or more new images.

A method of generating one or more new digital images using an original digitally-acquired image including a face is further provided. One or more groups of pixels may be identified that correspond to two or more faces within the original digitally-acquired image. A portion of the original image may be selected to include the group of pixels. Values of pixels may be automatically generated of one or more new images based on the selected portion in a manner which always includes at least one of the two or more faces within the one or more new images or a panning intermediate image between two of the faces of said two or more identified faces or a combination thereof.

Panning may be performed between the two or more identified faces. The panning may be from a first face to a second face of the two or more identified faces, and the second face may then be zoomed. The first face may be de-zoomed prior to panning to the second face. The second face may also be zoomed. The panning may include identifying a panning direction parameter between two of the identified faces. The panning may include sequencing along the identified panning direction between the two identified faces according to the identified panning direction parameter.

A method of digital image processing using face detection for achieving a desired spatial parameter is further provided including identifying a group of pixels that correspond to a face within a digital image, identifying one or more sub-groups of pixels that correspond to one or more facial features of the face, determining initial values of one or more parameters of pixels of the one or more sub-groups of pixels, determining an initial spatial parameter of the face within the digital image based on the initial values, and determining adjusted values of pixels within the digital image for adjusting the image based on a comparison of the initial and desired spatial parameters.

The initial spatial parameter may include orientation. The values of the pixels may be automatically adjusted within the digital image to adjust the initial spatial parameter approximately to the desired spatial parameter. An option may be automatically provided for adjusting the values of the pixels within the digital image to adjust the initial spatial parameter to the desired spatial parameter.

A method of digital image processing using face detection to achieve a desired orientation is also provided including identifying one or more groups of pixels that correspond to a face within a digital image, identifying one or more sub-groups of pixels that correspond to one or more facial features of the face, determining initial values of one or more parameters of pixels of the one or more sub-groups of pixels, determining an initial orientation of the face within the digital image based on the initial values, and determining adjusted values of pixels within the digital image for adjusting the orientation to the desired orientation.

Determining which of the sub-group of pixels belong to which of the group of face pixels may be performed. The determining of the initial values of one or more parameters of pixels may be calculated based on the spatial orientation of the one or more sub-groups that correspond to one or more facial features. The spatial orientation of the one or more sub-groups that correspond to one or more facial features may be calculated based on an axis of an ellipse fit to the sub-group. The adjusted values of pixels within the digital image may be rounded to a closest multiple of 90 degrees. The initial values may be adjusted to adjusted values for re-orienting the image to an adjusted orientation. The one or more facial features may include an eye, two eyes, two eyes and a mouth, an eye, a mouth, hairline, ears, nostrils, nose bridge, eyebrows neck as an extension of the face, or a nose, or combinations thereof, or otherwise as described above.

The method may include identifying one or more sub-groups of pixels that correspond to one or more facial features of the face. Initial values of one or more parameters of pixels of the one or more sub-groups of pixels may be determined. An initial spatial parameter of the face within the digital image may be determined based on the initial values. The initial spatial parameter may include any of orientation, size and location.

When the spatial parameter is orientation, values of one or more parameters of pixels may be adjusted for re-orienting the image to an adjusted orientation. The one or more facial features may include one or more of an eye, a mouth, two eyes, a nose, an ear, and other facial features including the neck as the physical extension of the face. The one or more facial features may include two or more features, and the initial orientation may be determined base on relative positions of the features that are determined based on the initial values. A shape such as a triangle may be generated for example between the two eyes and the center of the mouth, a golden rectangle as described above, or more generically, a polygon having points corresponding to preferably three or more features as vertices or axis.

Initial values of one or more chromatic parameters, such as color and tone, of pixels of the digital image may be determined. The values of one or more parameters may be automatically adjusted or an option to adjust the values to suggested values may be provided.

A method of digital image processing using face detection is also provided wherein a first group of pixels that correspond to a face within a digital image is identified, and a second group of pixels that correspond to another feature within the digital image is identified. A re-compositioned image is determined including a new group of pixels for at least one of the face and the other feature. The other feature may include a second face. The re-compositied image may be automatically generated or an option to generate the re-compositioned image may be provided. Values of one or more parameters of the first and second groups of pixels, and relative-adjusted values, may be determined for generating the re-compositioned image.

A method of compression of an image including a face is also provided also including identifying a group of pixels that correspond to a face within a digitally-acquired image. A first compression portion of the image including the group of pixels is determined. A second compression portion of the image other than the group of pixels is also determined. The first compression portion may be automatically compressed with higher-grade compression than the second compression portion to generate a compressed image including the face, or an option to provided the compressed image including the different grade compressions may be provided.

A method of determining the necessary resolution of an image including a face is also provided also including identifying a group of pixels that correspond to a face within a digitally-acquired image. A first resolution portion of the image including the group of pixels is determined. A second resolution portion of the image other than the group of pixels is also determined. The first resolution portion may be automatically compressed with higher-resolution than the second resolution portion to generate a rendered image including the face, or an option to provided the compressed image including the different grade resolution may be provided. Such method may be used to save on rendering time or consumables. For example, such method may determine using more ink on the more important regions of an image, and less ink on regions of less importance, this saving on the overall ink consumption when printing an image.

Each of the methods provided are preferably implemented within software and/or firmware either in the camera, the rendering device such as printers or display, or with external processing equipment. The software may also be downloaded into the camera or image processing equipment. In this sense, one or more processor readable storage devices having processor readable code embodied thereon are provided. The processor readable code programs one or more processors to perform any of the above or below described methods.

FIG. 1a illustrates a preferred embodiment. An image is opened by the application in block 102. The software then determines whether faces are in the picture as described in block 106. If no faces are detected, the software ceases to operate on the image and exits, 110.

Alternatively, the software may also offer a manual mode, where the user, in block 116 may inform the software of the existence of faces, and manually marks them in block 118. The manual selection may be activated automatically if no faces are found, 116, or it may even be optionally activated after the automatic stage to let the user, via some user interface to either add more faces to the automatic selection 112 or even 114, remove regions that are mistakenly 110 identified by the automatic process 118 as faces. Additionally, the user may manually select an option that invokes the process as defined in 106. This option is useful for cases where the user may manually decide that the image can be enhanced or corrected based on the detection of the faces. Various ways that the faces may be marked, whether automatically of manually, whether in the camera or by the applications, and whether the command to seek the faces in the image is done manually or automatically, are all included in preferred embodiments herein.

In an alternative embodiment, the face detection software may be activated inside the camera as part of the acquisition process, as described in Block 104. This embodiment is further depicted in FIG. 1b. In this scenario, the face detection portion 106 may be implemented differently to support real time or near real time operation. Such implementation may include sub-sampling of the image, and weighted sampling to reduce the number of pixels on which the computations are performed.

In an alternative embodiment, the face detection software may be activated inside the rendering device as part of the output process, as described in Block 103. This embodiment is further depicted in FIG. 1c. In this scenario, the face detection portion 106 may be implemented either within the rendering device, or within a en external driver to such device.

After the faces are tagged, or marked, whether manually as defined in 106, or automatically, 118, the software is ready to operate on the image based on the information generated by the face-detection stage. The tools can be implemented as part of the acquisition, as part of the post-processing, or both.

Block 120 describes panning and zooming into the faces. This tool can be part of the acquisition process to help track the faces and create a pleasant composition, or as a post processing stage for either cropping an image or creating a slide show with the image, which includes movement. This tool is further described in FIG. 6.

Block 130 depicts the automatic orientation of the image, a tool that can be implemented either in the camera as art of the acquisition post processing, or on a host software. This tool is further described in FIGS. 2a-2e.

Block 140 describes the way to color-correct the image based on the skin tones of the faces. This tool can be part of the automatic color transformations that occur in the camera when converting the image from the RAW sensor data form onto a known, e.g. RGB representation, or later in the host, as part of an image enhancement software. The various image enhancement operations may be global, affecting the entire image, such as rotation, and/or may be selective based on local criteria. For example, in a selective color or exposure correction as defined in block 140, a preferred embodiment includes corrections done to the entire image, or only to the face regions in a spatially masked operation, or to specific exposure, which is a luminance masked operation. Note also that such masks may include varying strength, which correlates to varying degrees of applying a correction. This allows a local enhancement to better blend into the image.

Block 150 describes the proposed composition such as cropping and zooming of an image to create a more pleasing composition. This tool, 150 is different from the one described in block 120 where the faces are anchors for either tracking the subject or providing camera movement based on the face location.

Block 160 describes the digital-fill-flash simulation which can be done in the camera or as a post processing stage. This tool is further described in FIGS. 4a-4e.

Alternatively to the digital fill flash, this tool may also be an actual flash sensor to determine if a fill flash is needed in the overall exposure as described in Block 170. In this case, after determining the overall exposure of the image, if the detected faces in the image are in the shadow, a fill flash will automatically be used. Note that the exact power of the fill flash, which should not necessarily be the maximum power of the flash, may be calculated based on the exposure difference between the overall image and the faces. Such calculation is well known to the one skilled in the art and is based on a tradeoff between aperture, exposure time, gain and flash power.

Figure 4A:
FIGS. 4a-4g illustrate digital fill-flash in accordance with one or more preferred embodiments.
Figure 4B:
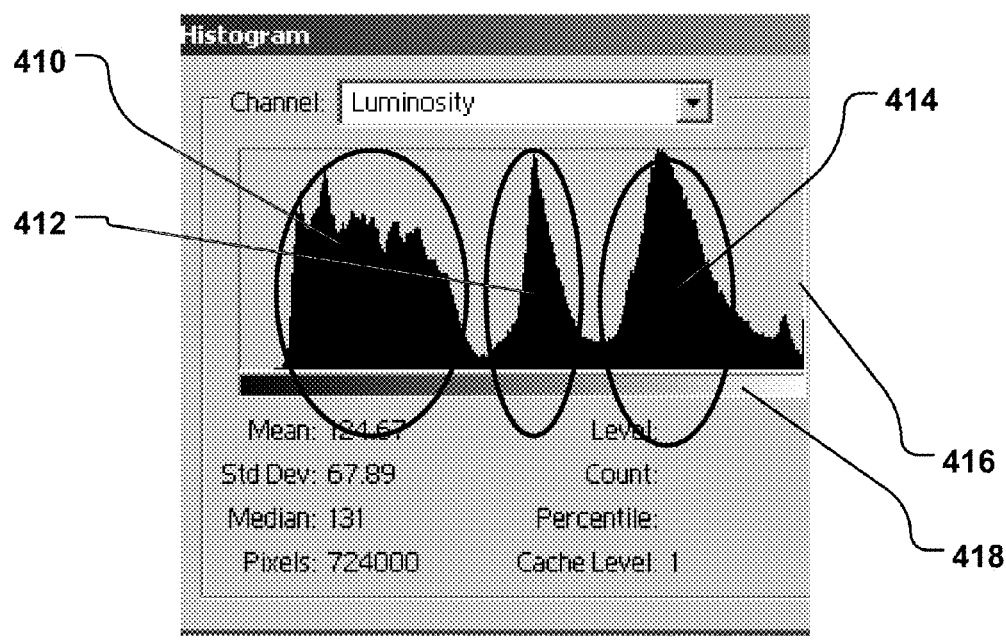
Figure 4C:
Figure 4D:
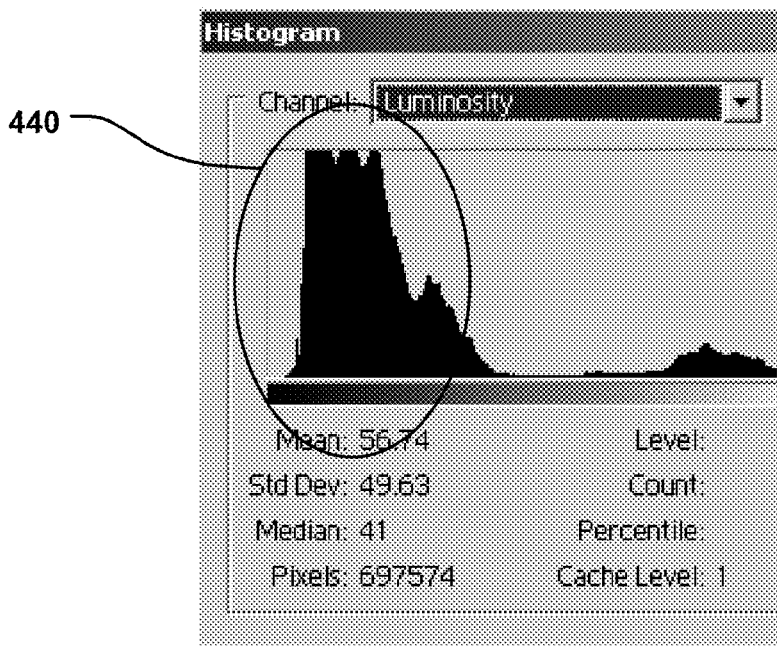
Figure 4E:
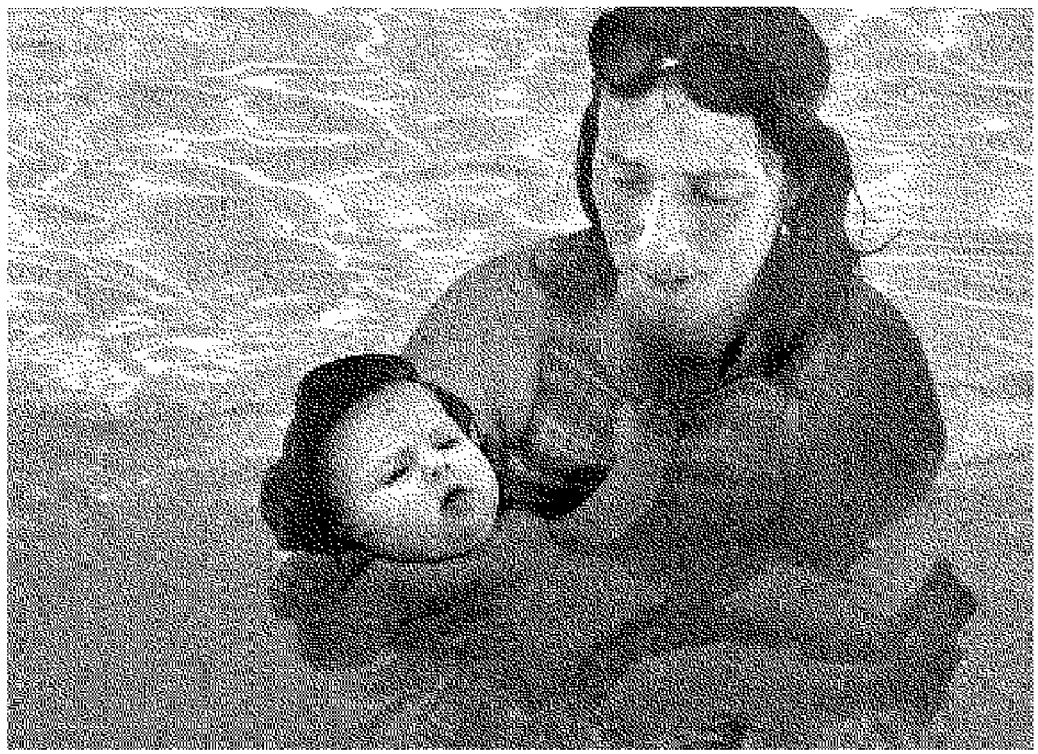
Figure 4F:
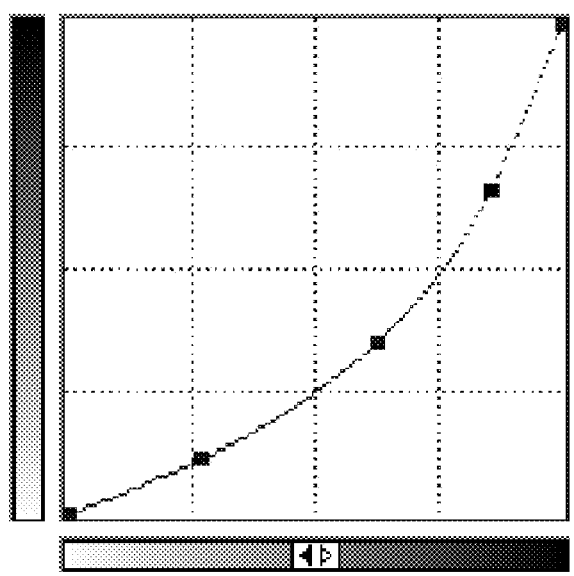

This tool is further described in FIG. 4e. Block 180 describes the ability of the camera to focus on the faces. This can be used as a pre-acquisition focusing tool in the camera, as further illustrated in FIG. 7.

Figure 1B:
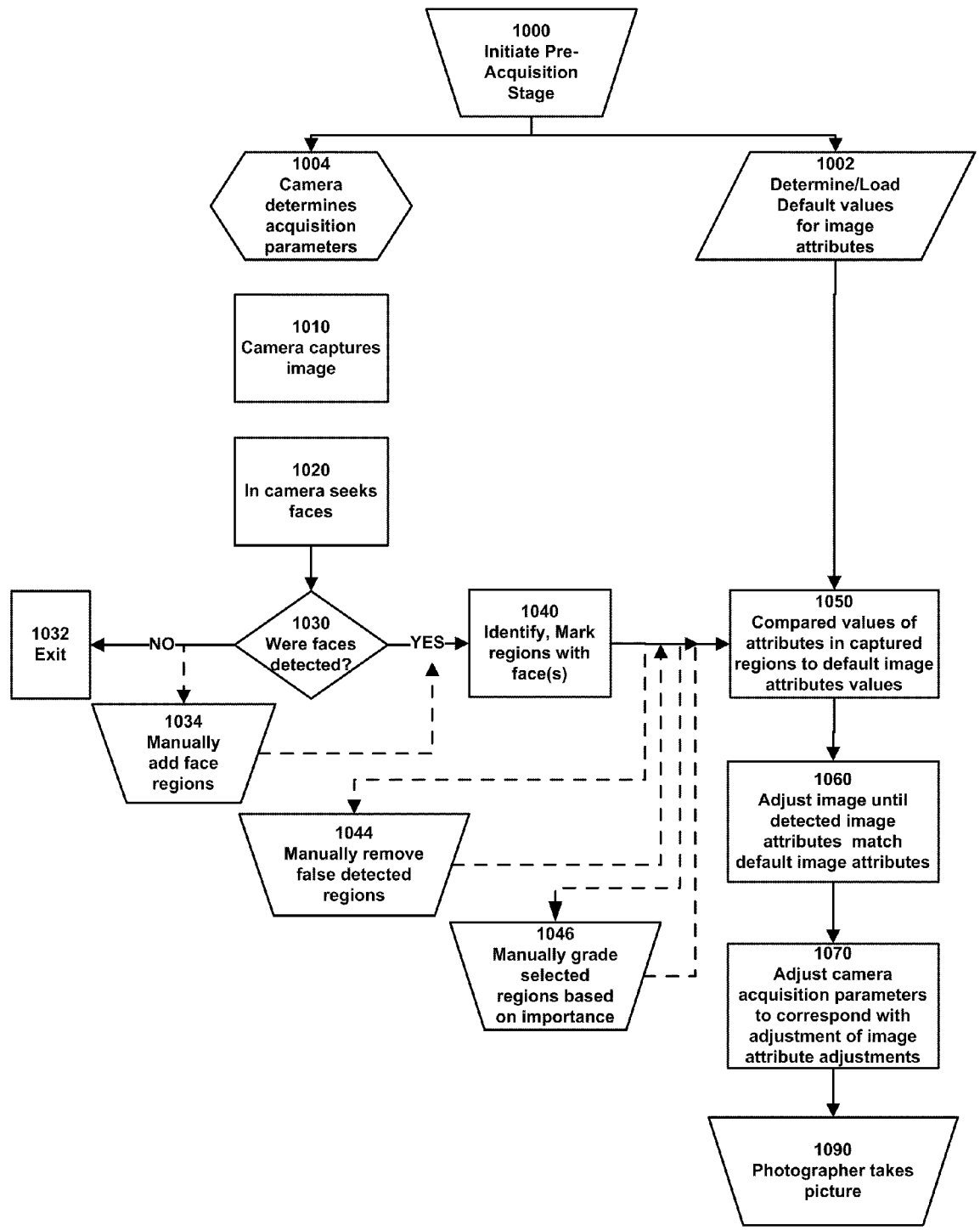
FIG. 1b illustrates a generic workflow of utilizing face information in an image to adjust image acquisition parameters in accordance with a preferred embodiment.

Referring to FIG. 1b, which describes a process of using face detection to improve in camera acquisition parameters, as aforementioned in FIG. 1a, block 106. In this scenario, a camera is activated, 1000, for example by means of half pressing the shutter, turning on the camera, etc. The camera then goes through the normal pre-acquisition stage to determine, 1004, the correct acquisition parameters such as aperture, shutter speed, flash power, gain, color balance, white point, or focus. In addition, a default set of image attributes, particularly related to potential faces in the image, are loaded, 1002. Such attributes can be the overall color balance, exposure, contrast, orientation etc.

An image is then digitally captured onto the sensor, 1010. Such action may be continuously updated, and may or may not include saving such captured image into permanent storage.

An image-detection process, preferably a face detection process, is applied to the captured image to seek faces in the image, 1020. If no images are found, the process terminates, 1032. Alternatively, or in addition to the automatic detection of 1030, the user can manually select, 1034 detected faces, using some interactive user interface mechanism, by utilizing, for example, a camera display. Alternatively, the process can be implemented without a visual user interface by changing the sensitivity or threshold of the detection process.

When faces are detected, 1040, they are marked, and labeled. Detecting defined in 1040 may be more than a binary process of selecting whether a face is detected or not, It may also be designed as part of a process where each of the faces is given a weight based on size of the faces, location within the frame, other parameters described herein, etc., which define the importance of the face in relation to other faces detected.

Alternatively, or in addition, the user can manually deselect regions, 1044 that were wrongly false detected as faces. Such selection can be due to the fact that a face was false detected or when the photographer may wish to concentrate on one of the faces as the main subject matter and not on other faces. Alternatively, 1046, the user may re-select, or empahsize one or more faces to indicate that these faces have a higher importance in the calculation relative to other faces. This process as defined in 1046, further defines the preferred identification process to be a continuous value one as opposed to a binary one. The process can be done utilizing a visual user interface or by adjusting the sensitivity of the detection process. After the faces are correctly isolated, 1040, their attributes are compared, 1050 to default values that were predefined in 1002. Such comparison will determine a potential transformation between the two images, in order to reach the same values. The transformation is then translated to the camera capture parameters, 1070, and the image, 1090 is acquired.

A practical example is that if the captured face is too dark, the acquisition parameters may change to allow a longer exposure, or open the aperture. Note that the image attributes are not necessarily only related to the face regions but can also be in relations to the overall exposure. As an exemplification, if the overall exposure is correct but the faces are underexposed, the camera may shift into a fill-flash mode as subsequently illustrated in FIG. 4a-4f.

Figure 1C:
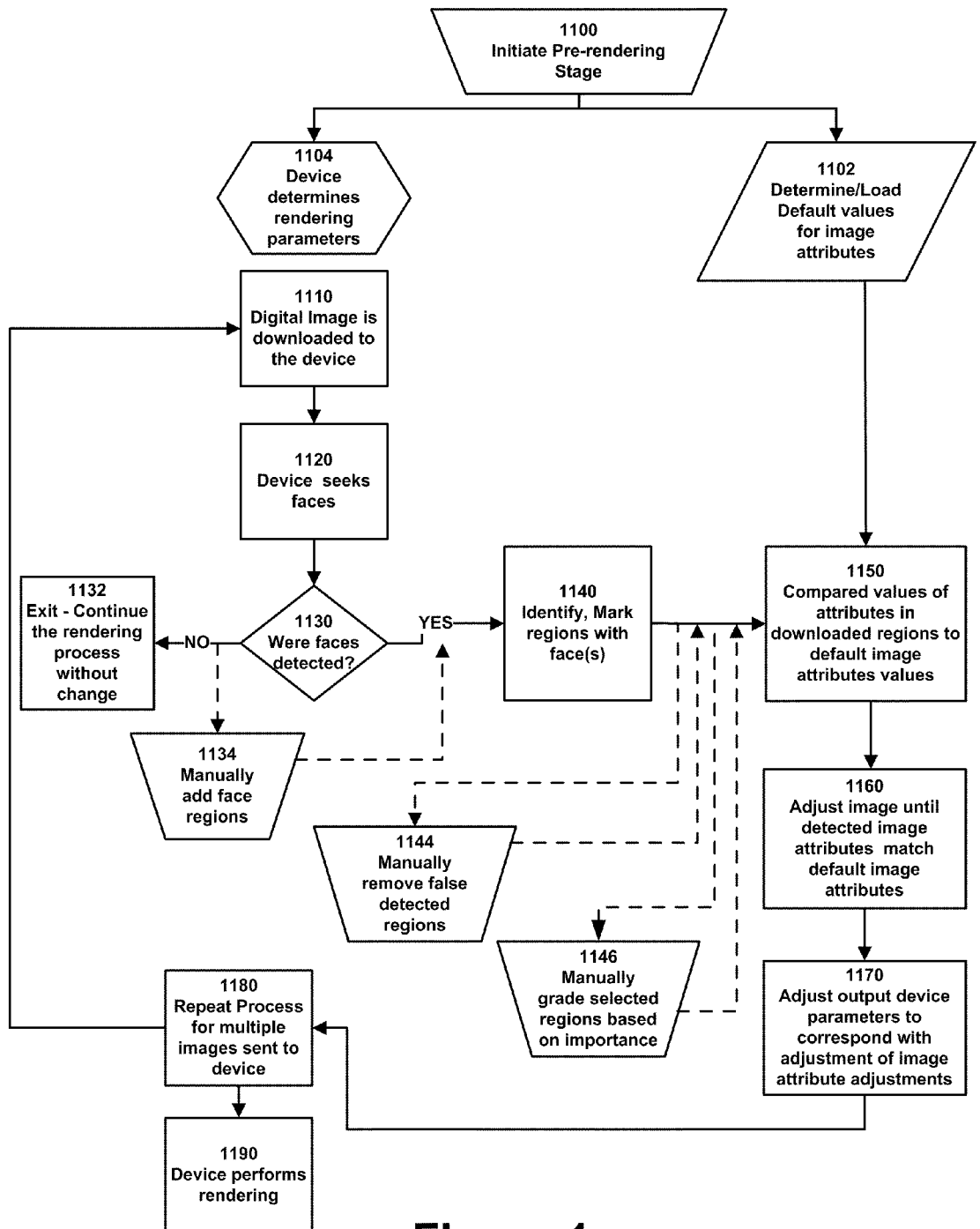
FIG. 1c illustrates a generic workflow of utilizing face information in a single or a plurality of images to adjust the image rendering parameters prior to outputting the image in accordance with a preferred embodiment.
Figure 2A:
Figure 2B:
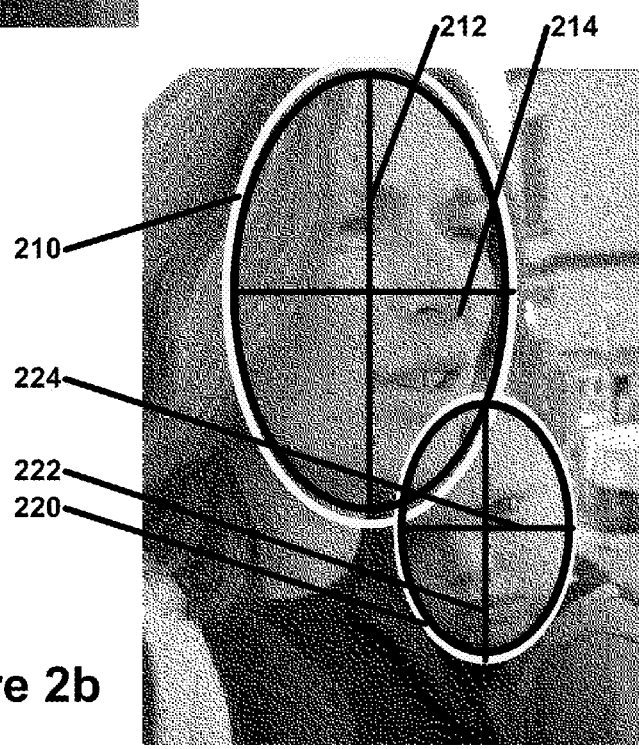
Figure 2E:
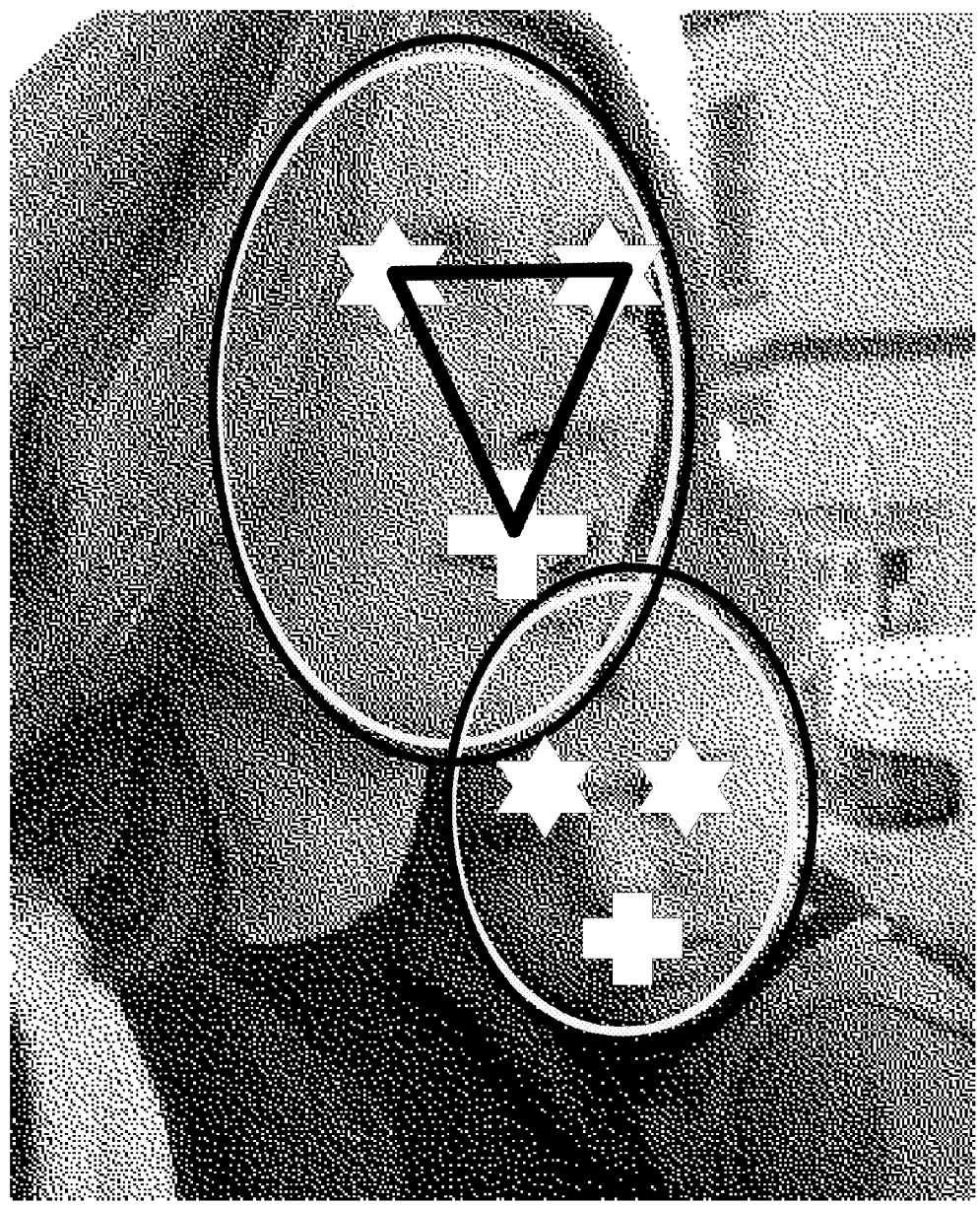

Referring to FIG. 1c, which describes a process of using face detection to improve output or rendering parameters, as aforementioned in FIG. 1a, block 103. In this scenario, a rendering device such as a printer or a display, herein referred to as the Device, activated, 1100. Such activation can be performed for example within a printer, or alternatively within a device connected to the printer such as a PC or a camera. The device then goes through the normal pre-rendering stage to determine, 1104, the correct rendering parameters such as tone reproduction, color transformation profiles, gain, color balance, white point and resolution. In addition, a default set of image attributes, particularly related to potential faces in the image, are loaded, 1102. Such attributes can be the overall color balance, exposure, contrast, orientation etc. An image is then digitally downloaded onto the device, 1110. An image-detection process, preferably a face detection process, is applied to the downloaded image to seek faces in the image, 1120. If no images are found, the process terminates, 1132 and the device resumes its normal rendering process. Alternatively, or in addition to the automatic detection of 1130, the user can manually select, 1134 detected faces, using some interactive user interface mechanism, by utilizing, for example, a display on the device. Alternatively, the process can be implemented without a visual user interface by changing the sensitivity or threshold of the detection process. When faces are detected, 1040, they are marked, and labeled. Detecting defined in 1140 may be more than a binary process of selecting whether a face is detected or not, It may also be designed as part of a process where each of the faces is given a weight based on size of the faces, location within the frame, other parameters described herein, etc., which define the importance of the face in relation to other faces detected.

Alternatively, or in addition, the user can manually deselect regions, 1144 that were wrongly false detected as faces. Such selection can be due to the fact that a face was false detected or when the photographer may wish to concentrate on one of the faces as the main subject matter and not on other faces. Alternatively, 1146, the user may re-select, or emphasize one or more faces to indicate that these faces have a higher importance in the calculation relative to other faces. This process as defined in 1146, further defines the preferred identification process to be a continuous value one as opposed to a binary one. The process can be done utilizing a visual user interface or by adjusting the sensitivity of the detection process. After the faces are correctly isolated, 1140, their attributes are compared, 1150 to default values that were predefined in 1102. Such comparison will determine a potential transformation between the two images, in order to reach the same values. The transformation is then translated to the device rendering parameters, 1170, and the image, 1190 is rendered. The process may include a plurality of images. In this case 1180, the process repeats itself for each image prior to performing the rendering process. A practical example is the creation of a thumbnail or contact sheet whish is a collection of low resolution images, on a single display instance.

A practical example is that if the face was too dark captured, the rendering parameters may change the tone reproduction curve to lighten the face. Note that the image attributes are not necessarily only related to the face regions but can also be in relations to the overall tone reproduction.

Referring to FIGS. 2a-2e, which describe the invention of automatic rotation of the image based on the location and orientation of faces, as highlighted in Figure-1 Block 130. An image of two faces is provided in FIG. 2a. Note that the faces may not be identically oriented, and that the faces may be occluding.

The software in the face detection stage, including the functionality of FIG. 1a, blocks 108 and 118, will mark the two faces, of the mother and son as an estimation of an ellipse 210 and 220 respectively. Using known mathematical means, such as the covariance matrix of the ellipse, the software will determine the main axis of the two faces, 212 and 222 respectively as well as the secondary axis 214 and 224. Even at this stage, by merely comparing the sizes of the axis, the software may assume that the image is oriented 90 degrees, in the case that the camera hel helo in landscape mode, which is horizontal, or in portrait mode which is vertical or +90 degrees, aka clockwise, or −90 degrees aka counter clockwise. Alternatively, the application may also be utilized for any arbitrary rotation value. However this information may not suffice to decide whether the image is rotated clockwise or counterclockwise.

FIG. 2c describes the step of extracting the pertinent features of a face, which are usually highly detectable. Such objects may include the eyes, 214, 216 and 224, 226, and the lips, 218 and 228. The combination of the two eyes and the center of the lips creates a triangle 230 which can be detected not only to determine the orientation of the face but also the rotation of the face relative to a facial shot. Note that there are other highly detectable portions of the image which can be labeled and used for orientation detection, such as the nostrils, the eyebrows, the hair line, nose bridge and the neck as the physical extension of the face etc. In this figure, the eyes and lips are provided as an example of such facial features Based on the location of the eyes if found, and the mouth, the image may, e.g., need to be rotated in a counter clockwise direction.

Note that it may not be enough to just locate the different facial features, but it may be necessary to compare such features to each other. For example, the color of the eyes may be compared to ensure that the pair of eyes originate form the same person. Another example is that in FIGS. 2-c and 2-d, if the software combined the mouth of 218 with the eyes of 226, 224, the orientation would have been determined as clockwise. In this case, the software detects the correct orientation by comparing the relative size of the mouth and the eyes. The above method describes means of determining the orientation of the image based on the relative location of the different facial objects. For example, it may be desired that the two eyes should be horizontally situated, the nose line perpendicular to the eyes, the mouth under the nose etc. Alternatively, orientation may be determined based on the geometry of the facial components themselves. For example, it may be desired that the eyes are elongated horizontally, which means that when fitting an ellipse on the eye, such as described in blocs 214 and 216, it may be desired that the main axis should be horizontal. Similar with the lips which when fitted to an ellipse the main axis should be horizontal. Alternatively, the region around the face may also be considered. In particular, the neck and shoulders which are the only contiguous skin tone connected to the head can be an indication of the orientation and detection of the face.

FIG. 2-e illustrates the image as correctly oriented based on the facial features as detected. In some cases not all faces will be oriented the same way. In such cases, the software may decide on other criteria to determine the orientation of the prominent face in the image. Such determination of prominence can be based on the relevant size of the faces, the exposure, or occlusion.

If a few criteria are tested, such as the relationship between different facial components and or the orientation of individual components, not all results will be conclusive to a single orientation. This can be due to false detections, miscalculations, occluding portions of faces, including the neck and shoulders, or the variability between faces. In such cases, a statistical decision may be implemented to address the different results and to determine the most likely orientation. Such statistical process may be finding the largest results (simple count), or more sophisticated ordering statistics such as correlation or principal component analysis, where the basis function will be the orientation angle. Alternatively or in addition, the user may manually select the prominent face or the face to be oriented. The particular orientation of the selected or calculated prominent face may itself be automatically determined, programmed, or manually determined by a user.

The process for determining the orientation of images can be implemented in a preferred embodiment as part of a digital display device. Alternatively, this process can be implemented as part of a digital printing device, or within a digital acquisition device.

The process can also be implemented as part of a display of multiple images on the same page or screen such as in the display of a contact-sheet or a thumbnail view of images. In this case, the user may approve or reject the proposed orientation of the images individually or by selecting multiple images at once. In the case of a sequence of images, this invention may also determine the orientation of images based on the information as approved by the user regarding previous images.

FIGS. 3a-3f describe an illustrative process in which a proposed composition is offered based on the location of the face. As defined in FIG. 1a blocks 108 and 118, the face 320 is detected as are one or more pertinent features, as illustrated in this case, the eyes 322 and 324. The location of the eyes are then calculated based on the horizontal, 330 and vertical 340 location. In this case, the face is located at the center of the image horizontally and at the top quarter vertically as illustrated in FIG. 3-d.

Based on common rules of composition and aesthetics, e.g., a face in a close up may be considered to be better positioned, as in FIG. 3-e if the eyes are at the ⅔rd line as depicted in 350, and ⅓ to the left or ⅓ to the right as illustrated in 360. Other similar rules may be the location of the entire face and the location of various portions of the face such as the eyes and lips based on aesthetic criteria such as the applying the golden-ratio for faces and various parts of the face within an image.

Figure 3A:
FIGS. 3a-3f illustrate an automatic composition and cropping of an image based on the location of the face in accordance with one or more preferred embodiments.
Figure 3B:
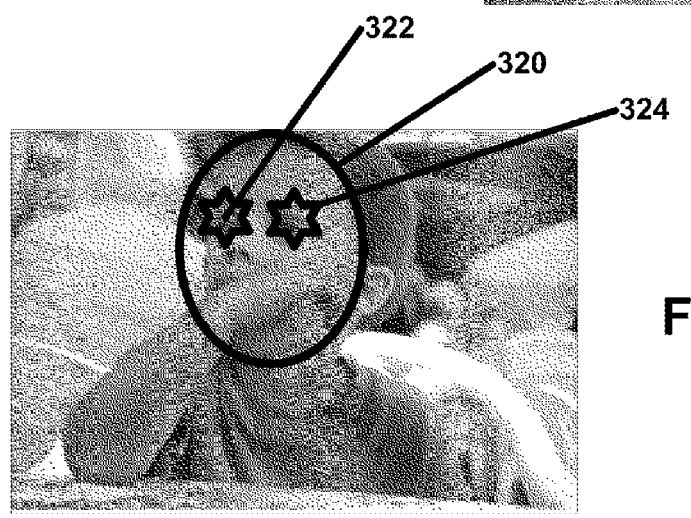
Figure 3C:
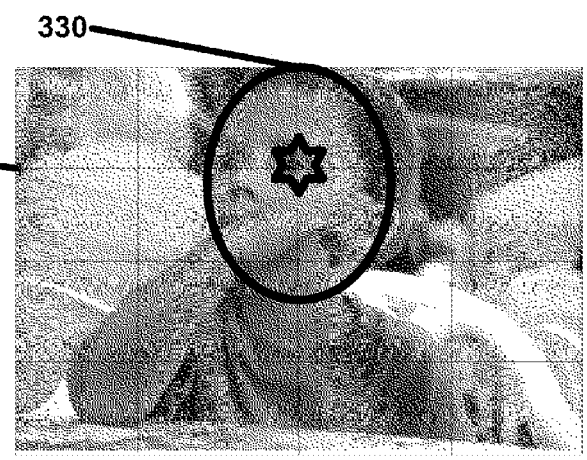
Figure 3D:
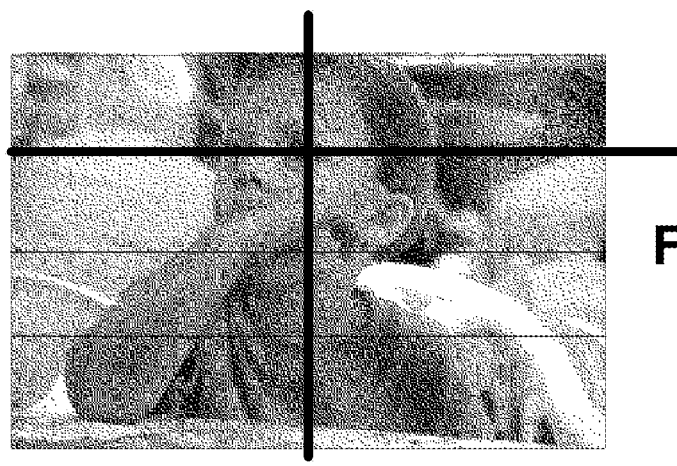
Figure 3E:
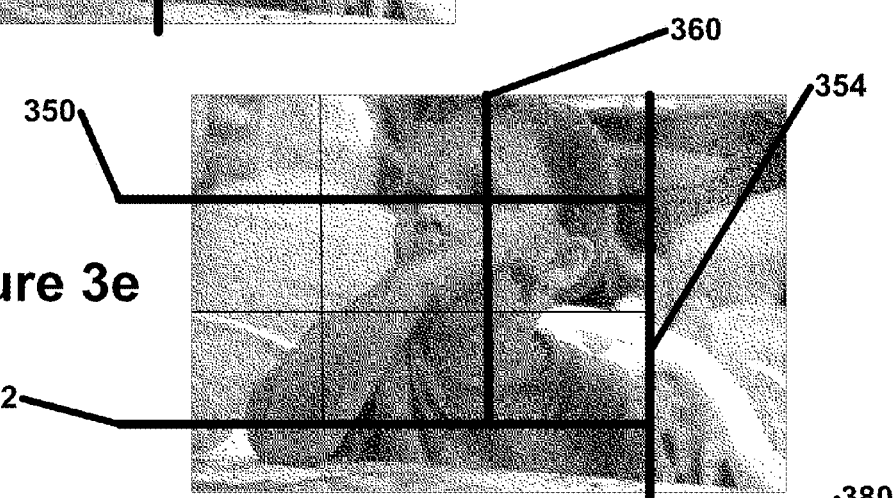
Figure 3F:

FIG. 3c introduces another aspect of face detection which may happen especially in non-restrictive photography. The faces may not necessarily be frontally aligned with the focal plane of the camera. In this figure, the object is looking to the side exposing partial frontal, or partial profile of the face. In such cases, the software may elect to use, the center of the face, which in this case may align with the left eye of the subject. If the subject was in full frontal position, the software may determine the center of the face to be around the nose bridge. The center of the face may be determined to be at the center of a rectangle, ellipse or other shape generally determined to outline the face or at the intersection of cross-hairs or otherwise as may be understood by those skilled in the art (see, e.g., ellipse 210 of FIGS. 2b-2e, ellipse 320 of FIG. 3b, ellipse 330 of FIG. 3c, the cross-hairs 350, 360 of FIG. 3e).

Based on the knowledge of the face and its pertinent features such as eyes, lips nose and ears, the software can either automatically or via a user interface that would recommend the next action to the user, crop portions of the image to reach such composition. For this specific image, the software will eliminate the bottom region 370 and the right portion 380. The process of re-compositioning a picture is subjective. In such case this invention will act as guidance or assistance to the user in determining the most pleasing option out of potentially a few. In such a case a plurality of proposed compositions can be displayed and offered to the user and the user will select one of them.

In an alternative embodiment, the process of re-compositioning the image can be performed within the image acquisition device as part of the image taking process, whether as a pre-capture, pre-acquisition or post acquisition stage. In this scenario the acquisition device may display a proposed re-compositioning of the image on its display. Such re-compositioning may be displayed in the device viewfinder or display similarly to FIG. 3*f*, or alternatively as guidelines of cropping such as lines 352 and 354. A user interface such will enable the user to select form the original composed image, or the suggested one. Similar functionality can be offered as part of the post acquisition or otherwise referred to the playback mode.

In additional embodiments, the actual lines of aesthetics, for example the $\frac{1}{3}^{rd}$ lines 350 and 350, may also be displayed to the use as assistance in determining the right composition. Referring to FIGS. 4*a*-4*f*, the knowledge of the faces may assist the user in creating an automatic effect that is otherwise created by a fill-flash. Fill-flash is a flash used where the main illumination is available light. In this case, the flash assists in opening up shadows in the image. Particularly, fill flash is used for images where the object in the foreground is in the shadow. Such instances occur for example when the sun is in front of the camera, thus casting a shadow on the object in the foreground. In many cases the object includes people posing in front of a background of landscape.

FIG. 4*a* illustrates such image. The overall image is bright due to the reflection of the sun in the water. The individuals in the foreground are therefore in the shadow.

A certain embodiment of calculating the overall exposure can be done using an exposure histogram. Those familiar in the art may decide on other means of determining exposure, any of which may be used in accordance with an alternative embodiment. When looking at the histogram of the luminance of the image at FIG. 4-*b*, there are three distinct areas of exposure which correspond to various areas. The histogram depicts the concentration of pixels, as defined by the Y-Axis 416, as a function of the different gray levels as defined by the X-axis 418. The higher the pixel count for a specific gray level, the higher the number as depicted on the y-axis. Regions 410 are in the shadows which belong primarily to the mother. The midtones in area 412 belong primarily to the shaded foreground water and the baby. The highlights 414 are the water. However, not all shadows may be in the foreground, and not all highlights may be in the background. A correction of the exposure based on the histogram may result in an unnatural correction.

When applying face detection, as depicted in FIG. 4-*c*, the histogram in FIG. 4-*d* may be substantially more clear. In this histogram, region 440 depicts the faces which are in the shadow. Note that the actual selection of the faces, as illustrated in 4-*c* need not be a binary mask but can be a gray scale mask where the boundaries are feathered or gradually changing. In addition, although somewhat similar in shape, the face region 440 may not be identical to the shadow region of the entire image, as defined, e.g., in FIG. 4*b* at area 410. By applying exposure correction as the face regions as illustrated in FIG. 4-*e*, such as passing the image through a lookup table

4-*f*, the effect is similar to the one of a fill flash that illuminated the foreground, but did not affect the background. By taking advantage of the gradual feathered mask around the face, such correction will not be accentuated and noticed. FIG. 4*e* can also be performed manually thus allowing the user to create a varying effect of simulated fill flash. Alternatively, the software may present the user with a selection of corrections based on different tone reproduction curves and different regions for the user to choose from.

Although exposure, or tone reproduction, may be the most preferred enhancement to simulate fill flash, other corrections may apply such as sharpening of the selected region, contrast enhancement, of even color correction. Additional advantageous corrections may be understood by those familiar with the effect of physical strobes on photographed images.

Figure 4G:
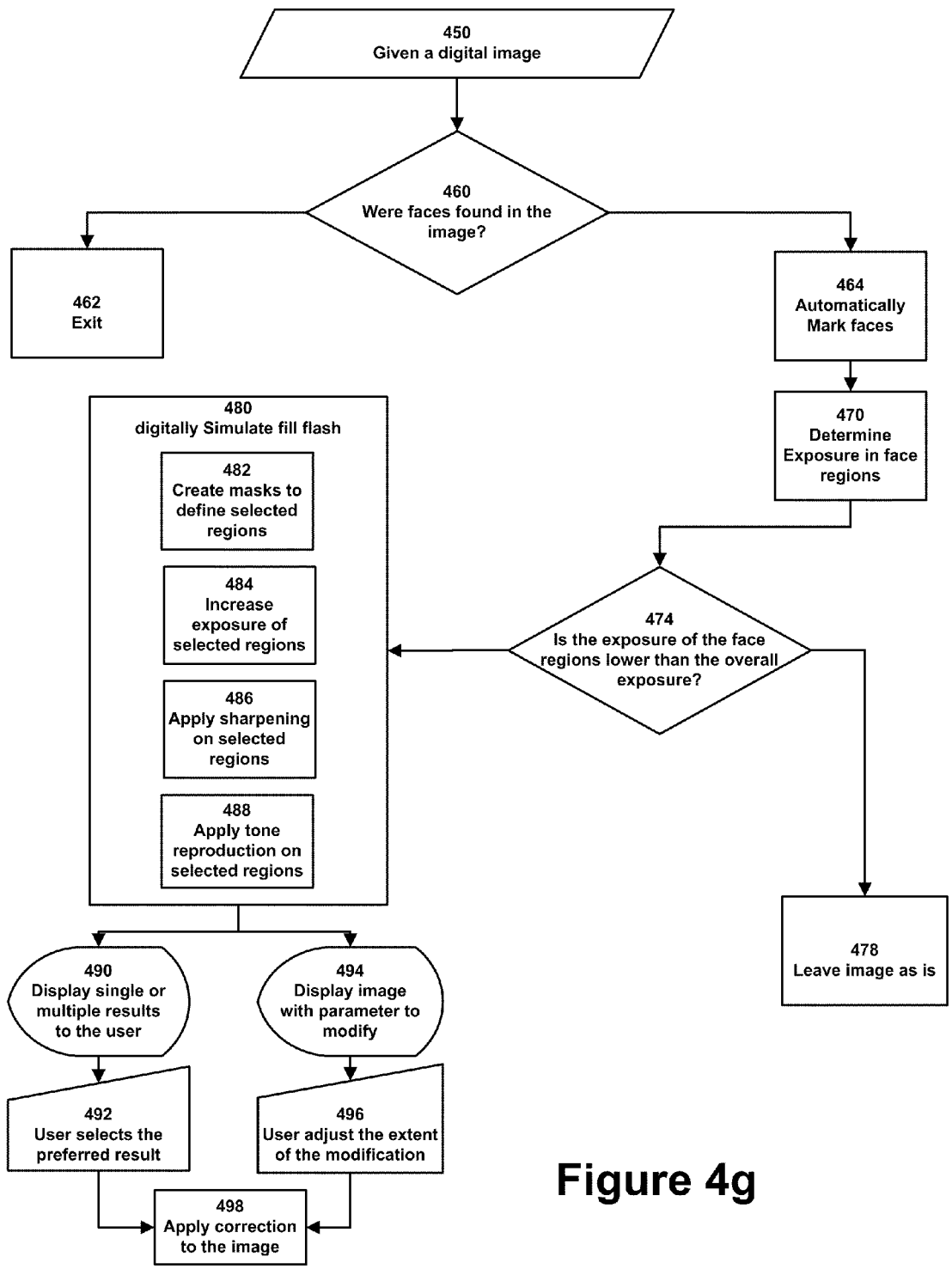
Figure 4H:
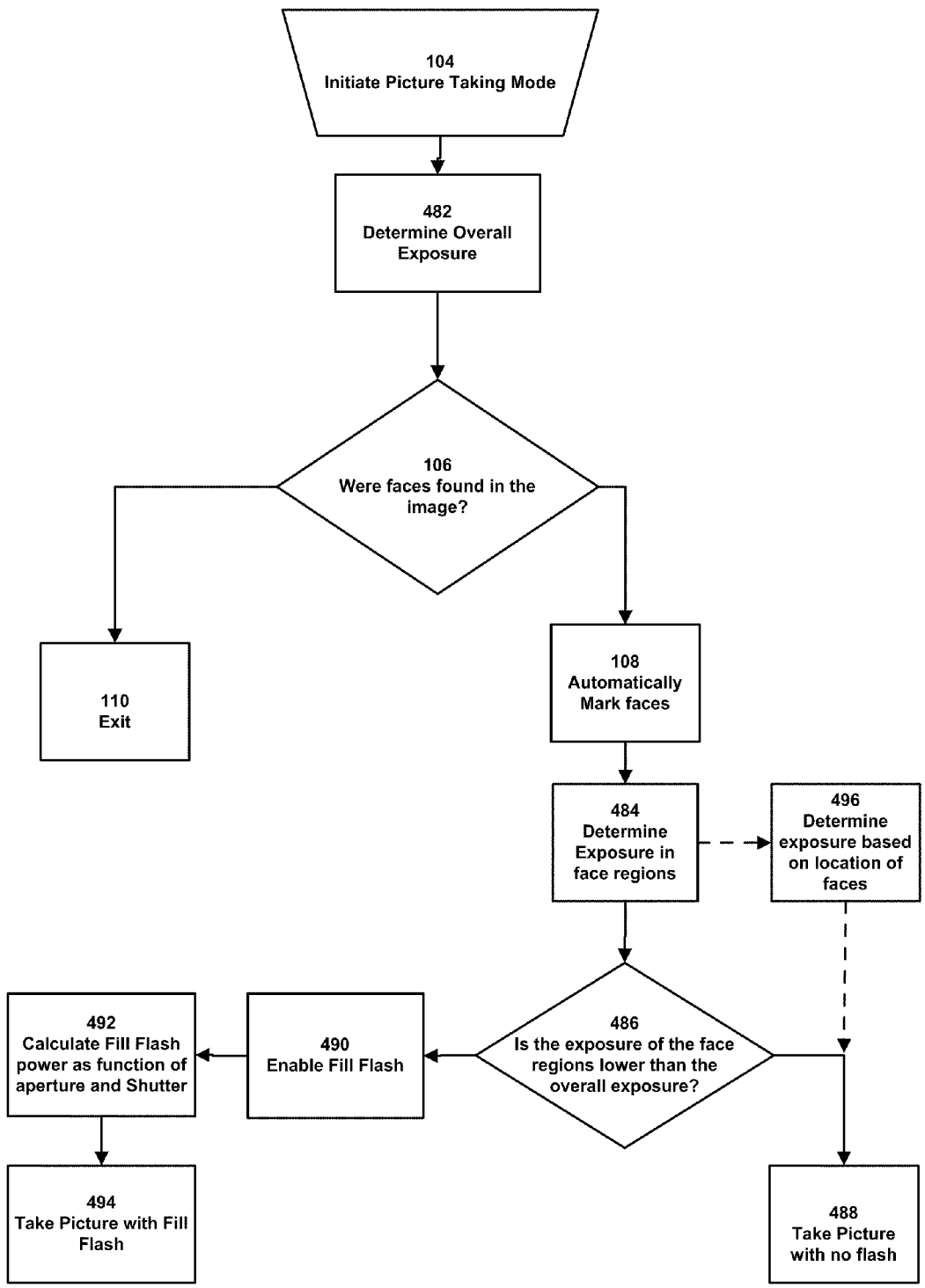
FIG. 4h describes an illustrative system in accordance with a preferred embodiment to determine in the camera as part of the acquisition process, whether fill flash is needed, and of so, activate such flash when acquiring the image based on the exposure on the face.

Alternatively, as described by the flow chart of FIG. 4*g*, a similar method may be utilized in the pre-acquisition stage, to determine if a fill flash is needed or not. The concept of using a fill flash is based on the assumption that there are two types of light sources that illuminate the image: an available external or ambient light source, which is controlled by the gain, shutter speed and aperture, and a flash which is only controlled by the flash power and affected by the aperture. By modifying the aperture vs. the shutter speed, the camera can either enhance the effect of the flash or decrease it, while maintaining the overall exposure. When the user activates the camera, in block 104, as defined in FIG. 1*a*, the camera calculates the overall exposure, 482. Such calculation is known to one skilled in the art and can be as sophisticated as needed. In block 108, the camera searched for the existence of faces in the image. An exposure is then calculated to the regions defined as belonging to the faces, 486. The disparity between the overall exposure as determined in 484 and the faces, 486 is calculated. If the face regions are substantially darker than the overall exposure 486, the camera will then activate the flash in a fill mode, 490, calculate the necessary flash power, aperture and shutter speed, 492 and acquire the image 494 with the fill flash. The relationship between the flash power, the aperture and the shutter speed are well formulated and known to one familiar in the art of photography. Examples of such calculations can be found in U.S. Pat. No. 6,151,073 to Steinberg et. al., hereby incorporated by reference.

Alternatively, in a different embodiment, 496, this algorithm may be used to simply determine the overall exposure based on the knowledge and the exposure of the faces. The image will then be taken, 488, based on the best exposure for the faces, as calculated in 496. Many cameras have a matrix type of exposure calculation where different regions receive different weights as to the contribution for the total exposure. In such cases, the camera can continue to implement the same exposure algorithm with the exception that now, regions with faces in them will receive a larger weight in their importance towards such calculations.

A technique in accordance with a preferred embodiment includes the detection of faces in a digital image. The skin tone and/or luminance of each detected face is determined. Preferably, a determination is also made of the luminance, color and/or tone of the background against which each face is set within the digital image. A separate determination is made for adjusting the luminance of and/or applying a fill flash to each detected face by a specific amount based on the luminance and/or skin tone of each particular face.

Figure 4I:
FIG. 4i shows a digital photograph including two faces of different skin tone, where the face with darker skin tone is also against a dark background.
Figure 4J:
FIG. 4j shows the digital photographs of FIG. 4i with greater fill-flash applied to the face with darker skin tone than to the face with lighter skin tone, if any.

FIG. 4*i* shows a digital photograph including two faces of different skin tone, where the face with darker skin tone is also against a dark background. FIG. 4*j* shows the digital photographs of FIG. 4i with greater fill-flash applied to the face with darker skin tone than to the face with lighter skin tone, if any.

Figure 4K:
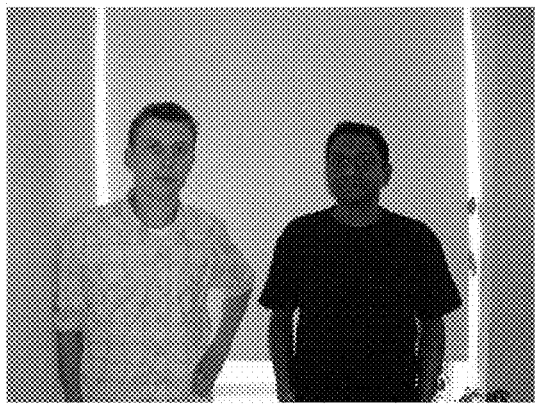
FIG. 4k shows a digital photograph including two faces of different skin tone, where the face with darker skin tone is also against a light background.
Figure 4L:
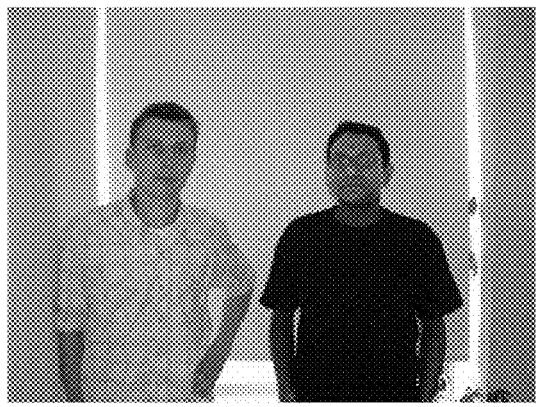
FIG. 4l shows the digital photographs of FIG. 4k with greater fill-flash applied to the face with darker skin tone than to the face with lighter skin tone, if any.

FIG. 4k shows a digital photograph including two faces of different skin tone, where the face with darker skin tone is also against a light background. FIG. 4l shows the digital photographs of FIG. 4k with greater fill-flash applied to the face with darker skin tone than to the face with lighter skin tone, if any.

Adobe Photoshop was used to apply additional fill flash to the dark face compared with that provided to the light face, if any. However, that product does not include Applicants' advantageous modules for detecting faces and skin tones of the faces, and for applying fill flash to each face in an amount, if any, that depends on the detected skin tone of each face. Applicants' module can also take into account the background against which each face is set in the image. FIG. 4i includes a darker of the two faces against a dark background, while FIG. 4k has the darker face against a light background. For each case, FIG. 4j for the dark background and FIG. 4l for the light background, the darker face is corrected with greater fill flash than the lighter face, and the background of the faces is taken into account in adjusting illumination of the two faces in the two images.

This advantageous method produces images of better quality especially for group photos with people belonging to different ethnic groups. When the image for a group of people belonging to different ethnic groups is taken, it can happen that some faces are not as visible as others because of differences in skin tone (see FIGS. 4i and 4k). To "correct" the image, preferably faces within the image are detected. In an alternative embodiment, it may be determined which ethnic groups that each face belongs to. For example, a separate input may be provided by a user for each detected face, or the face may be matched with another face image of the same person whose ethnicity has already been input. Based on a knowledge of an average luminance adjustment for a face belonging to a particular ethnic group, fill-flash or luminance adjusting may be provided. Appropriate local correction can be made to each face to make it more visible.

Figures 4M, 4N:
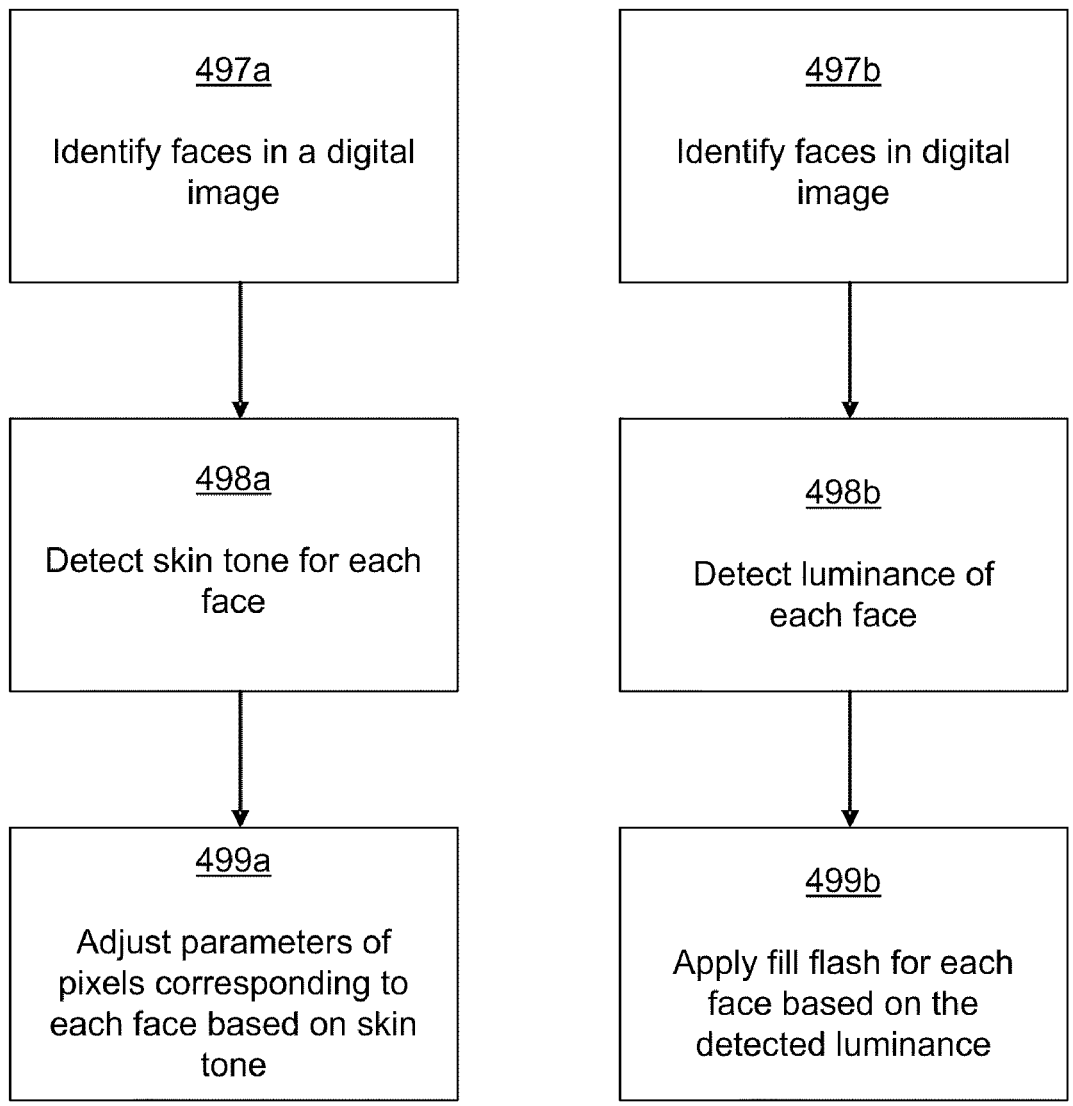
FIGS. 4m and 4n illustrate methods in accordance with a preferred embodiment.

FIG. 4m illustrates a method in accordance with a preferred embodiment. One face is identified or multiple faces are identified in a digital image at 497a. For each face, a skin tone is detected at 498a. Parameters of pixels corresponding to each face are adjusted or applied based on skin tone at 499a.

FIG. 4n illustrates a further method in accordance with a preferred embodiment. One face is identified or multiple faces are identified in a digital image at 497b. For each face, a luminance is detected at 498b. Fill-flash is applied or luminance otherwise adjusted for each face based on the detected luminance at 499b.

Figure 5:
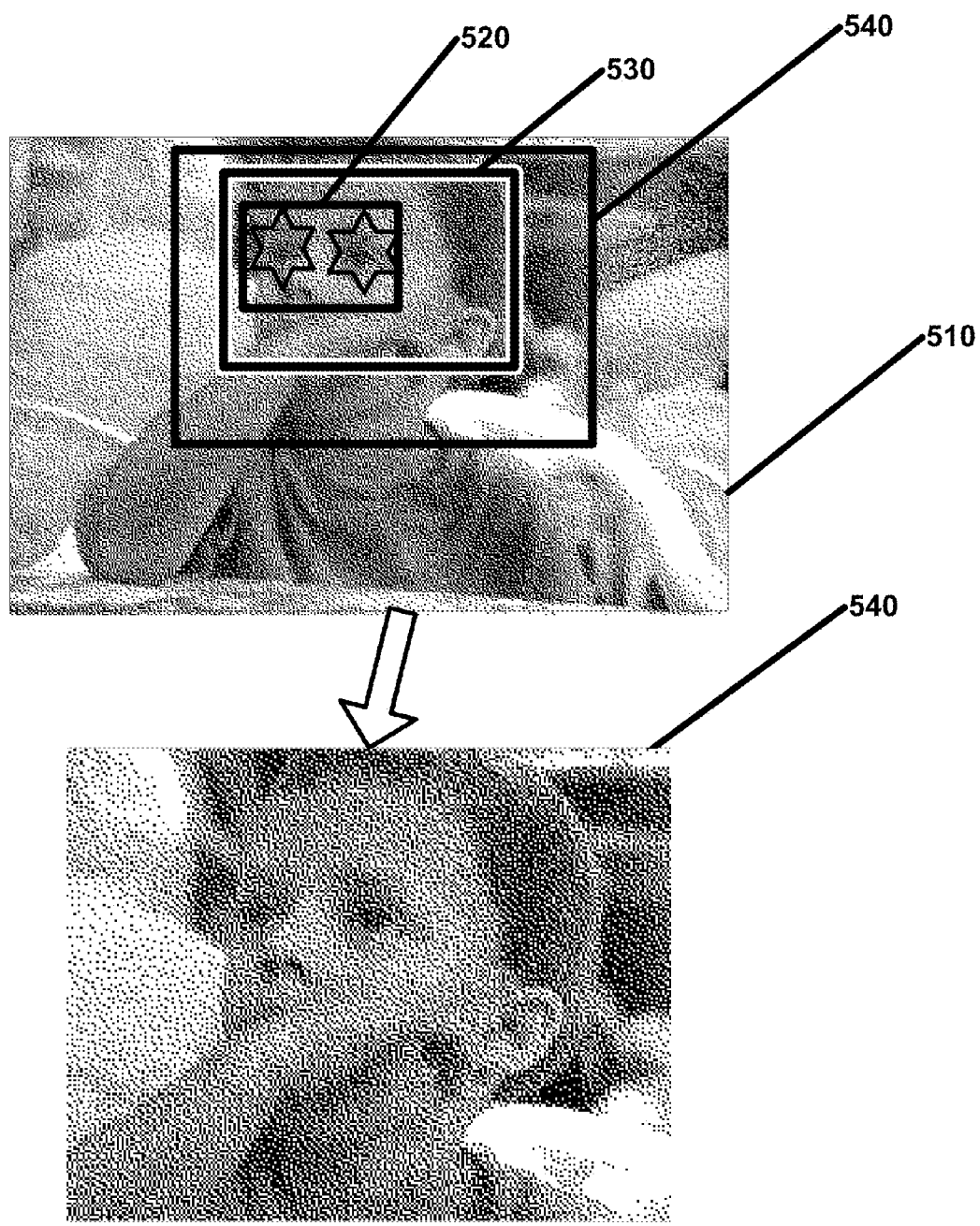
FIG. 5 illustrates the use of face-detection for generating dynamic slide shows, by applying automated and suggested zooming and panning functionality where the decision as to the center of the zoom is based on the detection of faces in the image.

FIG. 5 describes yet another valuable use of the knowledge of faces in images. In this example, knowledge of the faces can help improve the quality of image presentation. An image, 510 is inserted into a slide show software. The face is then detected as defined in FIG. 1 block 104, including the location of the important features of the face such as the eyes and the mouth.

Figure 6:
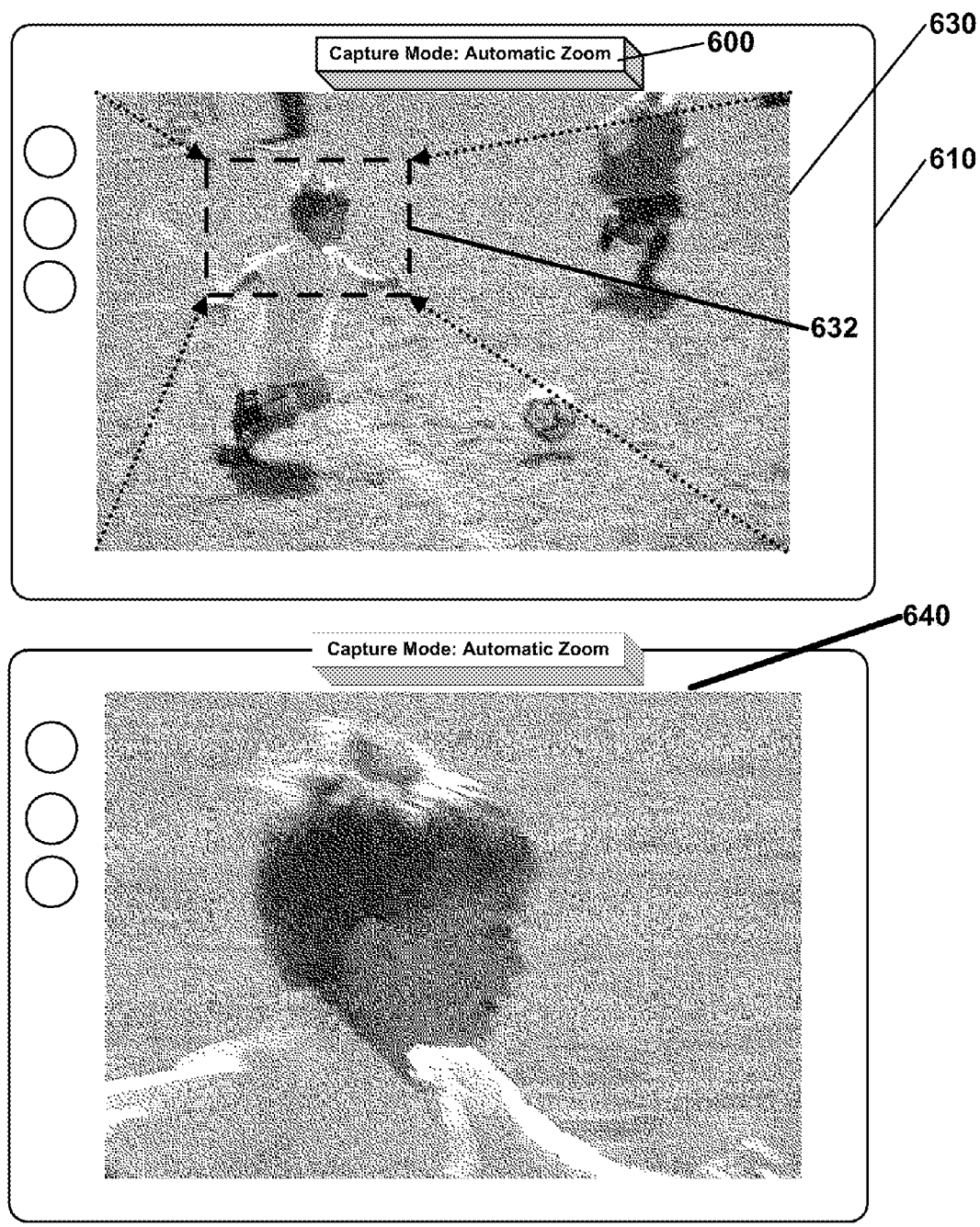
FIG. 6 describes an illustrative simulation of a viewfinder in a video camera or a digital camera with video capability, with an automatic zooming and tracking of a face as part of the live acquisition in a video camera, in accordance with a preferred embodiment.

The user can then choose between a few options such as: zoom into the face vs. zoom out of the face and the level of zoom for a tight close up 520, a regular close up 520 or a medium close up as illustrated by the bounding box 540. The software will then automatically calculate the necessary pan, tilt and zoom needed to smoothly and gradually switch between the beginning and the end state. In the case where more than one face is found, the software can also create a pan and zoom combination that will begin at one face and end at the other. In a more generic manner, the application can offer from within a selection of effects such as dissolve, FIG. 6 illustrates similar functionality but inside the device. A camera, whether still or video as illustrated by the viewfinder 610, when in auto track mode 600, can detect the faces in the image, and then propose a digital combination of zoom pan and tilt to move from the full wide image 630 to a zoomed in image 640. Such indication may also show on the viewfinder prior to zooming, 632 as indication to the user, which the user can then decide in real time whether to activate the auto zooming or not. This functionality can also be added to a tracking mode where the camera continuously tracks the location of the face in the image. In addition, the camera can also maintain the right exposure and focus based on the face detection.

Figure 7A:
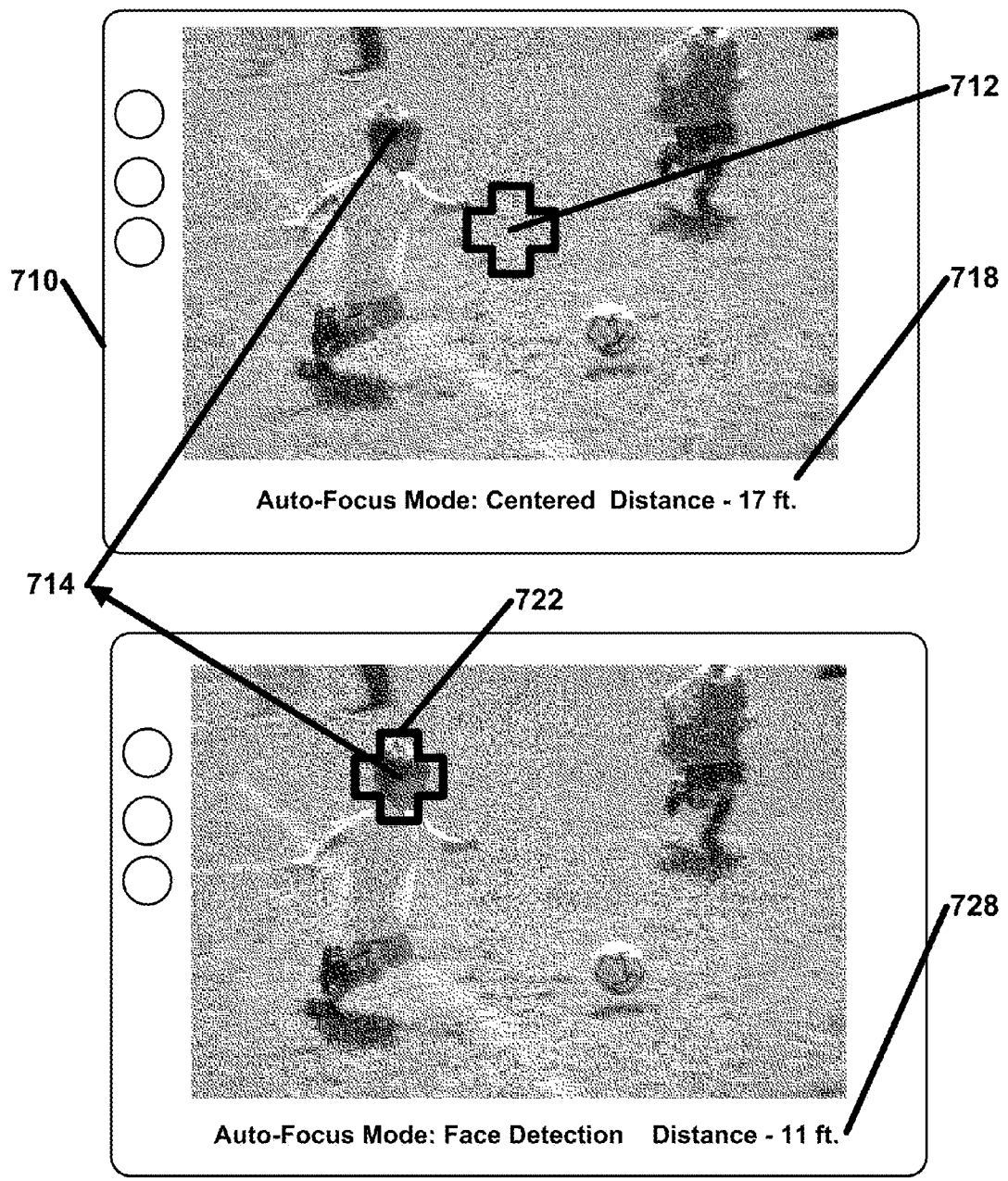
FIGS. 7a and 7b illustrate an automatic focusing capability in the camera as part of the acquisition process based on the detection of a face in accordance with one or more preferred embodiments.

FIG. 7a illustrates the ability to auto focus the camera based on the location of the faces in the image. Block 710 is a simulation of the image as seen in the camera viewfinder. When implementing a center weight style auto focus, 718, one can see that the image will focus on the grass, 17 feet away, as depicted by the cross 712. However, as described in this invention, if the camera in the pre-acquisition mode, 104 detects the face, 714, and focuses on the face, rather than arbitrarily on the center, the camera will then indicate to the user where the focus is, 722 and the lens will be adjusted to the distance to the face, which in this example, as seen in 728, is 11 ft. vs. the original 17 ft.

This process can be extended by one skilled in the art to support not only a single face, but multiple faces, by applying some weighted average. Such average will depend on the disparity between the faces, in distances, and sizes.

Figure 7B:
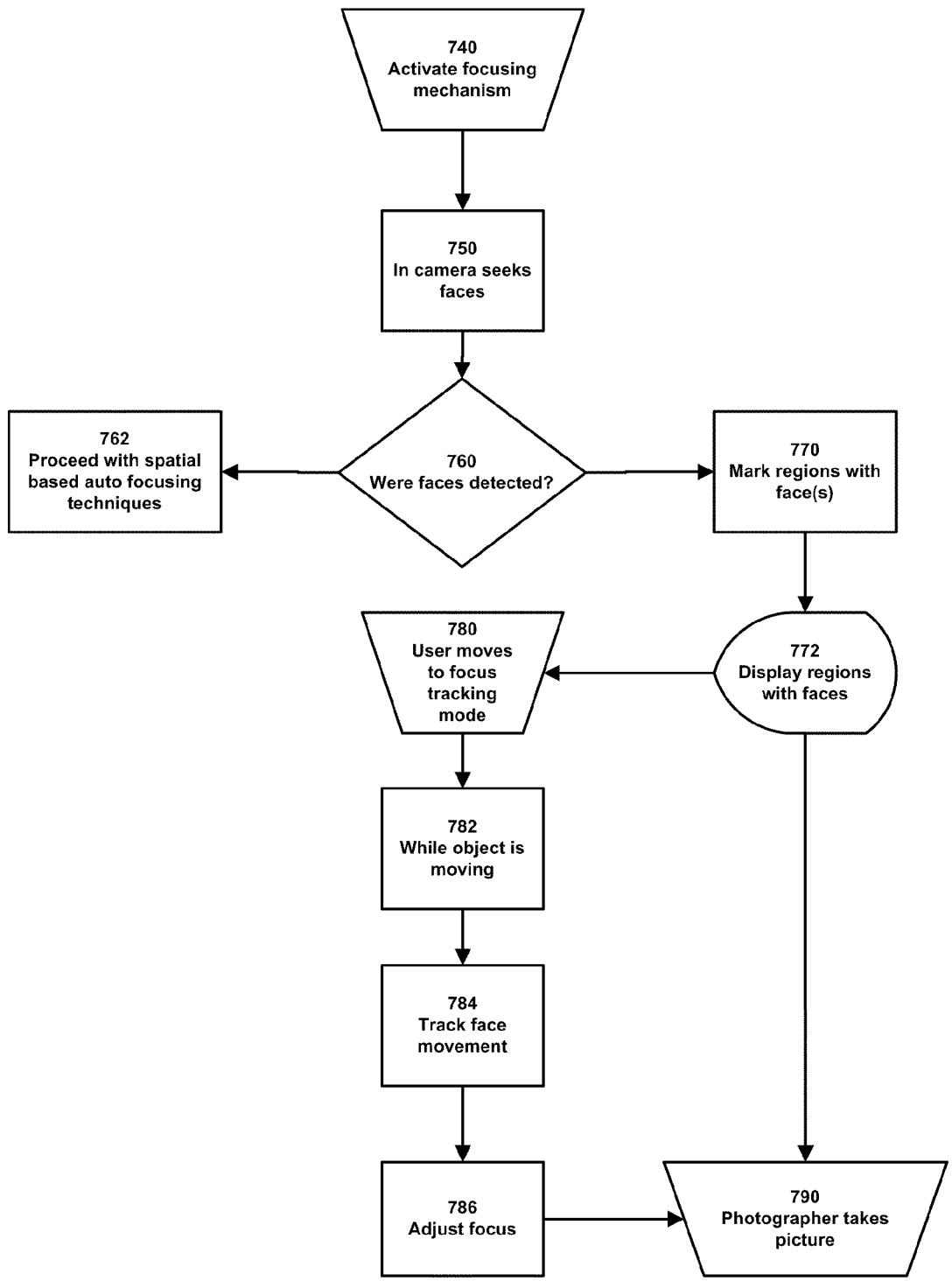

FIG. 7b presents the workflow of the process as illustrated via the viewfinder in FIG. 7-a. When the face-auto-focus mode is activated, 740, the camera continuously seeks for faces, 750. This operation inside the camera is performed in real time and needs to be optimized as such. If no faces are detected 760, the camera will switch to an alternative focusing mode, 762. If faces are detected, the camera will mark the single or multiple faces. Alternatively, the camera may display the location of the face 772, on the viewfinder or LCD. The user may then take a picture, 790 where the faces are in focus.

Alternatively, the camera may shift automatically, via user request or through preference settings to a face-tracking mode 780. In this mode, the camera keeps track of the location of the face, and continuously adjusts the focus based on the location of the face.

In an alternative embodiment, the camera can search for the faces and mark them, similarly to the cross in face 722. The photographer can then lock the focus on the subject, for example by half pressing the shutter. Locking the focus on the subject differs form locking the focus, by the fact that if the subject then moves, the camera can still maintain the correct focus by modifying the focus on the selected object.

Figure 8:
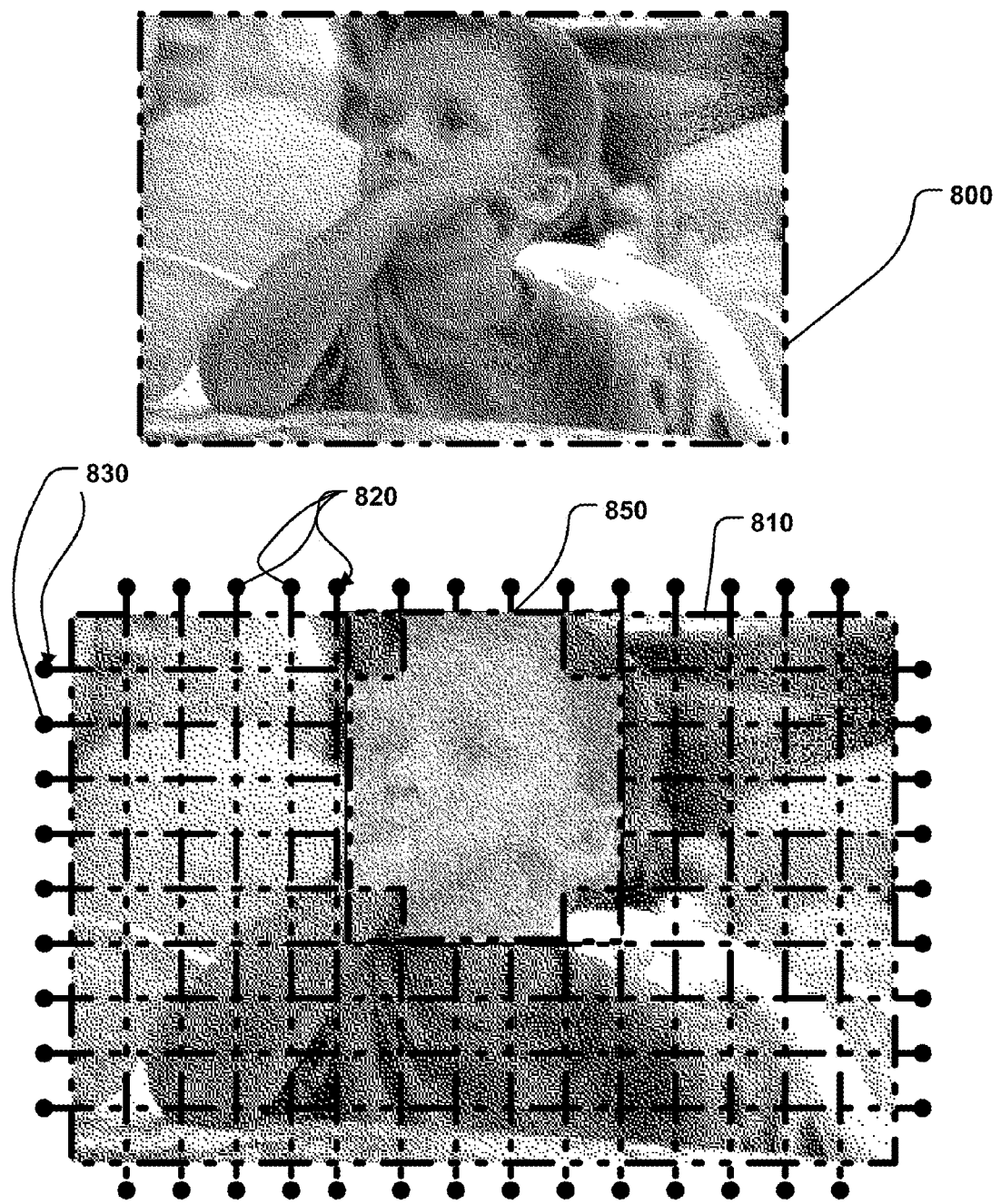
FIG. 8 illustrates an adjustable compression rate based on the location of faces in the image in accordance with a preferred embodiment.

FIG. 8 describes the use of information about the location and size of faces to determine the relevant compression ratio of different segments of the image. An image 800 may be segmented into tiles using horizontal grid 830 and vertical grid 820. The tiles which include or partially include face information are marked 850. Upon compression, regions of 850 may be compressed differently than the tiles of image 800 outside of this region. The degree of compression may be predetermined, pre-adjusted by the user or determined as an interactive process. In the case of multiple detected faces in an image, the user may also assign different quality values, or compression rates based on the importance of the faces in the image. Such importance may be determined subjectively using an interactive process, or objectively using parameters such as the relative size of the face, exposure or location of the face relative to other subjects in the image.

An alternative method of variable compression involves variable resolution of the image. Based on this, the method described with reference to FIG. 8 can also be utilized to create variable resolution, where facial regions which are preferably usually the important regions of the image, and will be preferably maintained with higher overall resolution than other regions in the image. According to this method, referring to FIG. 8, the regions of the face as defined in block 850 will be preferably maintained with higher resolution than regions in the image 800 which are not part of 850.

An image can be locally compressed so that specific regions will have a higher quality compression which equates to lower compression rate. Alternatively and/or correspondingly, specific regions of an image may have more or less information associated with them. The information can be encoded in a frequency-based, or temporal-based method such as JPEG or Wavelet encoding. Alternatively, compression on the spatial domain may also involve a change in the image resolution. Thus, local compression may also be achieved by defining adjustable variable resolution of an image in specific areas. By doing so, selected or determined regions of importance may maintain low compression or high resolution compared with regions determined to have less importance or non-selected regions in the image.

Face detection and face tracking technology, particularly for digital image processing applications according to preferred and alternative embodiments set forth herein, are further advantageous in accordance with various modifications of the systems and methods of the above description as may be understood by those skilled in the art, as set forth in the references cited and incorporated by reference herein and as may be otherwise described below. For example, such technology may be used for identification of faces in video sequences, particularly when the detection is to be performed in real-time. Electronic component circuitry and/or software or firmware may be included in accordance with one embodiment for detecting flesh-tone regions in a video signal, identifying human faces within the regions and utilizing this information to control exposure, gain settings, auto-focus and/or other parameters for a video camera (see, e.g., U.S. Pat. Nos. 5,488,429 and 5,638,136 to Kojima et al., each hereby incorporated by reference). In another embodiment, a luminance signal and/or a color difference signal may be used to detect the flesh tone region in a video image and/or to generate a detecting signal to indicate the presence of a flesh tone region in the image. In a further embodiment, electronics and/or software or firmware may detect a face in a video signal and substitute a "stored" facial image at the same location in the video signal, which may be useful, e.g., in the implementation of a low-bandwidth videophone (see, e.g., U.S. Pat. No. 5,870,138 to Smith et al., hereby incorporated by reference).

In accordance with another embodiment, a human face may be located within an image which is suited to real-time tracking of a human face in a video sequence (see, e.g., U.S. Pat. Nos. 6,148,092 and 6,332,033 to Qian, hereby incorporated by reference). An image may be provided including a plurality of pixels and wherein a transformation and filtering of each pixel is performed to determine if a pixel has a color associated with human skin-tone. A statistical distribution of skin tones in two distinct directions may be computed and the location of a face within the image may be calculated from these two distributions.

In another embodiment, electrical and/or software or firmware components may be provided to track a human face in an image from a video sequence where there are multiple persons (see, e.g., U.S. Pat. No. 6,404,900 also to Qian, hereby incorporated by reference). A projection histogram of the filtered image may be used for output of the location and/or size of tracked faces within the filtered image. A face-like region in an image may also be detected by applying information to an observer tracking display of the auto-stereoscopic type (see, e.g., U.S. Pat. No. 6,504,942 to Hong et al., incorporated by reference).

An apparatus according to another embodiment may be provided for detection and recognition of specific features in an image using an eigenvector approach to face detection (see, e.g., U.S. Pat. No. 5,710,833 to Moghaddam et al., incorporated by reference). Additional eigenvectors may be used in addition to or alternatively to the principal eigenvector components, e.g., all eigenvectors may be used. The use of all eigenvectors may be intended to increase the accuracy of the apparatus to detect complex multi-featured objects.

Another approach may be based on object identification and recognition within a video image using model graphs and/or bunch graphs that may be particularly advantageous in recognizing a human face over a wide variety of pose angles (see, e.g., U.S. Pat. No. 6,301,370 to Steffens et al., incorporated by reference). A further approach may be based on object identification, e.g., also using eigenvector techniques (see, e.g., U.S. Pat. No. 6,501,857 to Gotsman et al., incorporated by reference). This approach may use smooth weak vectors to produce near-zero matches, or alternatively, a system may employ strong vector thresholds to detect matches. This technique may be advantageously applied to face detection and recognition in complex backgrounds.

Another field of application for face detection and/or tracking techniques, particularly for digital image processing in accordance with preferred and alternative embodiments herein, is the extraction of facial features to allow the collection of biometric data and tracking of personnel, or the classification of customers based on age, sex and other categories which can be related to data determined from facial features. Knowledge-based electronics and/or software or firmware may be used to provide automatic feature detection and age classification of human faces in digital images (see, e.g., U.S. Pat. No. 5,781,650 to Lobo & Kwon, hereby incorporated by reference). Face detection and feature extraction may be based on templates (see U.S. Pat. No. 5,835,616 also to Lobo & Kwon, incorporated by reference). A system and/or method for biometrics-based facial feature extraction may be employed using a combination of disparity mapping, edge detection and filtering to determine co-ordinates for facial features in the region of interest (see, e.g., U.S. Pat. No. 6,526,161 to Yan, incorporated by reference). A method for the automatic detection and tracking of personnel may utilize modules to track a users head or face (see, e.g., U.S. Pat. No. 6,188,777, incorporated by reference). For example, a depth estimation module, a color segmentation module and/or a pattern classification module may be used. Data from each of these modules can be combined to assist in the identification of a user and the system can track and respond to a user's head or face in real-time.

The preferred and alternative embodiments may be applied in the field of digital photography. For example, automatic determination of main subjects in photographic images may be performed (see, e.g., U.S. Pat. No. 6,282,317 to Luo et al., incorporated by reference). Regions of arbitrary shape and size may be extracted from a digital image. These may be grouped into larger segments corresponding to physically coherent objects. A probabilistic reasoning engine may then estimate the region which is most likely to be the main subject of the image.

Faces may be detected in complex visual scenes and/or in a neural network based face detection system, particularly for digital image processing in accordance with preferred or alternative embodiments herein (see, e.g., U.S. Pat. No. 6,128,397 to Baluja & Rowley; and "Neural Network-Based Face Detection," IEEE Transactions on Pattern Analysis and Machine Intelligence, Vol. 20, No. 1, pages 23-28, January 1998 by the same authors, each reference being hereby incorporated by reference. In addition, an image may be rotated prior to the application of the neural network analysis in order to optimize the success rate of the neural-network based detection (see, e.g., U.S. Pat. No. 6,128,397, incorporated by reference). This technique is particularly advantageous when faces are oriented vertically. Face detection in accordance with preferred and alternative embodiments, and which are particularly advantageous when a complex background is involved, may use one or more of skin color detection, spanning tree minimization and/or heuristic elimination of false positives (see, e.g., U.S. Pat. No. 6,263,113 to Abdel-Mottaleb et al., incorporated by reference).

A broad range of techniques may be employed in image manipulation and/or image enhancement in accordance with preferred and alternative embodiments, may involve automatic, semi-automatic and/or manual operations, and are applicable to several fields of application. Some of the discussion that follows has been grouped into subcategories for ease of discussion, including (i) Contrast Normalization and Image Sharpening; (ii) Image Crop, Zoom and Rotate; (iii) Image Color Adjustment and Tone Scaling; (iv) Exposure Adjustment and Digital Fill Flash applied to a Digital Image; (v) Brightness Adjustment with Color Space Matching; and Auto-Gamma determination with Image Enhancement; (vi) Input/Output device characterizations to determine Automatic/Batch Image Enhancements; (vii) In-Camera Image Enhancement; and (viii) Face Based Image Enhancement.

(i) Contrast Normalization and Image Sharpening

This field is relates to adjusting a digital image, after capture, to improve the image sharpness, contrast and/or potentially simulate an improved focus on the main subject. An image may be sharpened by transforming the image representation into a frequency-domain representation and by selectively applying scaling factors to certain frequency domain characteristics of an image (see, e.g., U.S. Pat. No. 6,421,468 to Ratnakar et al., incorporated by reference). The modified frequency domain representation may be back-transformed into the spatial domain and provide a sharpened version of the original image. This image sharpening effect may be applied to the entire image (see particularly Ratnakar et al., above). Image sharpening may also be applied selectively to particular spatial regions within an image in accordance with an embodiment herein.

Automatic contrast enhancement of an image may be provided by increasing the dynamic range of the tone levels within an image without causing substantial distortion or shifts to the color map of the image (see, e.g., U.S. Pat. No. 6,393,148 to Bhaskar, incorporated by reference). This enhancement may be applied to the entire image or selectively and advantageously to one or more particular spatial regions within the image. In addition, correction for the entire image may be selectively derived from characteristics of a particular spatial region within the image, such as a human face region.

A digital photo-finishing system may include image processing to provide scene balance, image sharpening and/or contrast normalization (see, e.g., U.S. Pat. No. 6,097,470 to Buhr et al., incorporated by reference). Algorithms may be optimized to a print medium and applied to the entire image.

(ii) Crop, Zoom and Rotate a Digital Image

The selection of a portion of a digital image with an improved compositional form over the original image represents a form of image enhancement by "cropping". A similar technique involves selecting a sub-region of the original image and enhancing the resolution of this sub-region by interpolating between the pixels. This represents a form of digital zooming of the image and can provide an improvement on the original image if correctly applied. A third means of spatially altering the image is to change the image orientation by rotating the image. This may be, e.g., a straightforward 90° or 270° rotation to change the image aspect from landscape to portrait or vice-versa, or may involve a rotation of an arbitrary number of degrees, e.g., to level the eye line, etc. (see also above).

An electrical system, software or firmware may be provided wherein an image of a portion of a photographic image is automatically produced. This may utilize a technique known as a "belief map" (see, e.g., US patent application 2002/0114535 to Luo, incorporated by reference) to determine the probability that a certain region within the principle image is the main region of interest. Main subjects may be automatically determined in an image (see, e.g., U.S. Pat. No. 6,282,317 to Luo et al., incorporated by reference). Regions of arbitrary shape and/or size may be extracted from a digital image. These regions may be grouped into larger segments corresponding to physically coherent objects. A probabilistic reasoning engine for main-subject-detection may also estimate the region which is most likely to be the main subject of the image. This technique may involve a set of feature extractions from the original image which are then filtered through a tunable, extensible, probability network to generate the belief map. In this alternative embodiment, the probabilistic "belief map" is generated by the main subject detection engine.

The above system of the alternative embodiment involving the generation of a belief map may generally involve some degree of computational complexity. According to a preferred embodiment herein, information gained from the detection and/or presence of faces in an image may be advantageously used to determine a region or regions of interest within an image, generally involving a reduction of computational complexity and making its application with resource-constrained portable or embedded systems very desirable.

A system, software and/or firmware may be provided that automatically rotates, crops and scales digital images for printing (see, e.g., U.S. Pat. No. 6,456,732 to Kimbell et al., incorporated by reference). In this embodiment, an optimal number of digital images may be fit onto a sheet of paper of definite size in a printer. The system may or may not involve improving the images themselves, and/or may include one or more components that serve to preserve the original image quality in the printed form. In accordance with a preferred embodiment, the actions of rotating, cropping and/or scaling an image may be based on criteria other than those derived from the image as a whole, such as information pertaining to faces in the image.

An embodiment involving automatic image cropping may use regional intensity variations to separate areas of an image with uniform intensity levels from those with significant variation in intensity levels (see, e.g., U.S. Pat. No. 5,978,519 to Bollman et al.). A portrait, e.g., may be cropped from a uniform background, such as in the instance of a passport photograph. In accordance with a preferred embodiment, however, a portrait may be extracted from a more complex background. Automatic cropping may be based on intensity and/or texture variances of regions within an image. Face detection is preferably used as an advantageous means to determine a region within an image for automatic cropping.

In the context of automatic image rotation, and determining image orientation, an embodiment including electrical, software and/or firmware components that detect blue sky within images may be included (see, e.g., U.S. Pat. No. 6,504, 951 to Luo et al., incorporated by reference) This feature allows image orientation to be determined once the blue-sky region(s) are located and analyzed in an image. In accordance with an alternative embodiment, other image aspects are also used in combination with blue sky detection and analysis, and in particular the existence of facial regions in the image, to determine the correct orientation of an image.

(iii) Color Adjustment and Tone Scaling of a Digital Image

A portion of an image may be modified in accordance with colorimetric parameters (see, e.g., US published patent application 2002/0105662 to Patton et al., incorporated by reference). Such image modification may involve identifying a region representing skin tone in an image, displaying a plurality of renderings for the skin tone, selecting one of the renderings and/or modifying the skin tone regions in the images in accordance with the rendering of the skin tone, e.g., as selected by the user or automatically or semi-automatically selected using software and/or firmware. The skin tone information from a particular region of the image may be used to enhance the image. In accordance with a preferred embodiment, facial regions are detected within the image, based on which image enhancement is automatically or semi-automatically performed.

In another embodiment, image color may be compensated when adjusting the contrast of a digital color image (see, e.g., U.S. Pat. No. 6,438,264 to Gallagher et al.). This may include receiving a tone scale function, calculating a local slope of the tone scale function for each pixel of a digital image, calculating a color saturation signal from the digital color image, and/or adjusting the color saturation signal for each pixel of the color image based on the local tone scale slope. Image enhancements may be applied to the entire image and/or may be based on a global tone scale function. In accordance with the preferred embodiment, such enhancement may be applied to a region of interest such as a facial region. Characteristics of a region of the image may be used to apply automatic enhancements to the entire image or, alternatively, the use of whole image characteristics or global characteristic functions may be used to apply automatic enhancements to selective regions of an image, such as facial regions.

A spatially blurred and/or sub-sampled version of an original image can be used to obtain information regarding statistical characteristics of a scene or original image (see, e.g., U.S. Pat. No. 6,249,315 to Holm, incorporated by reference). This information may be combined with tone reproduction curves and other characteristics of an output device or media to provide an enhancement strategy for optimized output of a digital image. This processing can be performed automatically or by simple, intuitive manual adjustment by a user.

(iv) Exposure Adjustment and Digital Fill Flash

A system, software, firmware or method for simulating fill flash in digital photography may be provided in accordance with preferred and alternative embodiments herein (see also US patent application 2003/0052991 to Stavely et al.) A digital camera may be used to shoot a series of photographs of a scene at various focal distances. These pictures may be subsequently analyzed to determine distances to different objects in the scene. Regions of these pictures may have their brightness selectively adjusted based on the aforementioned distance calculations and may be then combined to form a single, photographic image. In accordance with a preferred embodiment, information regarding the existence of facial regions within the image is used, e.g., to particularly selectively adjust the brightness of the facial regions. Moreover, automatic enhancement on a single image may be advantageously performed in the preferred embodiment. Performing such enhancement on a single image reduces the speed which a camera may otherwise need to be capture multiple images. Alternatively, several images may be combined to form one. A multiplicity of images may be captured in this alternative embodiment by a digital camera without the camera moving, generally involving a camera employing a very fast image capture process.

Another embodiment includes scene recognition method and a system using brightness and ranging mapping (see, e.g., US published patent application 2001/0031142 to Whiteside, incorporated by reference). Auto-ranging and/or brightness measurement may be used to adjust image exposure to ensure that background and/or foreground objects are correctly illuminated in a digital image. Automatically adjustment of image exposure may be performed prior to image capture, or more preferably after the image is captured.

In the preferred embodiment, corrections and enhancements of regions within digital images are performed preferably including entire faces or parts of faces that themselves form part of an overall image. This may include a selected face or selected faces of multiple faces appearing in an image. For these preferred corrections and enhancements, fill flash is preferably used. Alternatively, image correction and enhancements may be performed on entire digital images. This may involve correction of image exposure and tone scale (see, e.g., U.S. Pat. No. 6,473,199 to Gilman et al. and U.S. Pat. No. 5,991,456 to Rahman et al., incorporated by reference).

Regional analysis and regional adjustment of image intensity or exposure levels may be performed in accordance with preferred and alternative embodiments. A method or apparatus may use area selective exposure adjustment (see, e.g., U.S. Pat. No. 5,818,975 to Goodwin et al., incorporated by reference). A digital image can have the dynamic range of its scene brightness reduced to suit the available dynamic brightness range of an output device by separating the scene into two regions: one with a high brightness range and one with a low brightness range. A brightness transform may be derived for both regions to reduce the brightness of the first region and to boost the brightness of the second region, recombining both regions to reform an enhanced version of the original image for an output device.

In another embodiment, brightness adjustment of images uses digital scene analysis (see, e.g., U.S. Pat. No. 5,724,456 to Boyack et al.). An image may be partitioned into blocks and larger groups of blocks, that may be referred to as sectors. An average luminance block value may be determined. A difference may be determined between the maximum and minimum block values for one or more sectors. If this difference exceeds a pre-determined threshold, the sector may be marked active. A histogram of weighted counts of active sectors against average luminance sector values may also be plotted and the histogram shifted to using a pre-determined criteria so that the average luminance sector values of interest will fall within a destination window corresponding to a tonal reproduction capability of a destination application or output device. In accordance with a preferred embodiment, regions within an image are preferably used, and even more preferably the presence or knowledge of a human facial region or facial regions within the image are used to determine and/or apply image enhancement and/or correction to the regions or to the image as whole.

(v) Brightness Adjustment; Color Space Matching; Auto-Gamma

Further preferred and alternative embodiments involving face detection and image enhancement may include brightness adjustment and color matching between color spaces. For example, image data may be transformed from device dependent color spaces to device-independent lab color spaces and back again (see, e.g., U.S. Pat. No. 6,459,436 to Kumada et al., incorporated by reference). Image data may be initially captured in a color space representation which is dependent on the input device, and may be subsequently converted into a device independent color space. Gamut mapping (hue restoration) may be performed in the device independent color space and the image data may then be mapped back to a second device-dependent color space and sent to an output device.

A system, software and/or firmware may be provided to correct luminance and chrominance data in digital color images (see, e.g., U.S. Pat. No. 6,268,939 to Klassen et al., incorporated by reference). In this embodiment, transformations may be optimized between device dependent and device independent color spaces by applying sub-sampling of the luminance and chrominance data. In another embodiment, quality improvement of a printed image may be performed by automatically determining an image gamma and then adjusting the gamma of a printer to correspond to that of the image (see, e.g., U.S. Pat. No. 6,192,149 to Eschback et al., incorporated by reference). The printed quality of a digital image may be thereby enhanced, and preferably a digital image itself may also be enhanced in this way. In an alternative embodiment, software or firmware provides for automatically determining the gamma of a digital image. This information may be advantageously used to directly adjust image gamma, or used as a basis for applying other enhancements to the original digital image, such as face detection-based image enhancement according to a preferred embodiment. In addition, a gradation correction to an RGB image signal may be implemented allowing image brightness to be adjusted without affecting image hue and saturation (see, e.g., U.S. Pat. No. 6,101,271 to Yamashita et al.).

(vii) In-Camera Image Enhancement

In further preferred and alternative embodiments, improvements to a digital image may be suggested to a user after the image has been acquired or captured by a camera (see, e.g., U.S. Pat. No. 6,516,154 to Parulski et al., incorporated by reference). According to these embodiments, a user may crop, re-size and/or adjust color balance either before saving a picture or before deciding to re-save or delete the picture. The user may choose to re-take a picture using different settings on the camera. Suggestion for improvements may be made by the camera user-interface.

(viii) Face-Based Image Enhancement

In preferred embodiments herein, automatically or semi-automatically improving the appearance of faces in images based on automatically and/or manually detecting such facial images in the digital image is an advantageous feature (see also US published patent application 20020172419, to Lin et al., incorporated by reference). Lightness contrast and color level modification of an image may be performed to produce better results. Moreover, using such information and other information for detecting orientation, providing assistance as part of an in-camera acquisition process, and/or providing assistance in a composition or a slide show based on such information are features of preferred and alternative embodiments herein. The application may automatically detect the faces, or suggest portions of an image that may correspond to faces for confirmation and selection by a user, and the software or firmware may allow the user to select additional image portions that may correspond to faces not detected by the automatic or semi-automatic processes of the software. Image enhancement according to preferred and alternative embodiment herein may be applied to a face region or face regions only, or the enhancement may be applied to the entire image, or selective and distinct corrections may be applied to both background and foreground regions, particularly facial regions, based on knowledge of the presence of faces in the image and/or other image regions such as blue sky or other detectable features.

Auto-Focus

In accordance with a preferred embodiment, detection of a face or a primary face among multiple faces in an image enhances the ability of the software and/or firmware of an image processing system, within a camera or external to a camera, is advantageously used to provide an accurate focusing on the appropriate subjects. Distances to subjects may be estimated, and automatic or manual determinations may be made as to where the main subject matter exists.

A system, software and/or firmware may include an exposure measurement and/or focus detection feature that uses an image sensor such as photo diode array (MOS image sensor), or CCD (charge coupled device) (see, e.g., U.S. Pat. Nos. 4,047,187, and RE31370, to Mashimo et al., incorporated by reference). In general with respect to preferred and alternative embodiments, a photodetector array device may be used for the detection of images for image processing, particularly preferably including faces and face detection, or from which the image may be acquired and/or captured and stored for image processing. A system may defines an active auto focus system in which a beam of modulated energy is projected towards a subject to be focused upon with the energy reflected therefrom directed towards the detector array. An auto focus circuit for a video or still camera may also include passive systems that do not use infra red signal reflections for auto-focus (see, e.g., U.S. Pat. Nos. 4,638,364 and RE33682, incorporated by reference). Such systems may be based on analysis of images either based on high frequency information, or alternatively a local contrast calculation (see, e.g., U.S. Pat. No. 4,638,364 and Japanese patent JP 5,260,360 A2, incorporated by reference).

A subject of an image, such as a facial region, may be based on a center-weighted formula. Alternatively, a camera may focus on objects based on the direction that the eye which is looking into the viewfinder is pointing (see, e.g., U.S. Pat. No. 5,291,234, incorporated by reference). Such alternative system may generally further include special additional hardware in the camera viewfinder. The system of the preferred embodiment which detects faces and generally utilized software and/or firmware to determine auto-focus based on size and/or location of one or more primary faces is advantageous over this alternative hardware-based auto-focus system in that eye movement may involve not only a fixation where the photographer holds his/her gaze at a stationary point, but may involve saccade where the photographer moves his/her gaze quickly between a few points. Also according to a preferred embodiment, electronic detection, acquisition and/or capture circuitry, software and firmware serves to detect and/or correct or enhance a focus of an image, preferably automatically or alternatively semi-automatically as providing a choice or choices to a user to select from, based on an analysis of the content of the image, and in particular based on the location of faces in the image which may be deemed to have primary importance among various regions on the image.

Selecting Regions of Interest

In further embodiments, various schemes may be used for selecting an area or areas of interest from an electronically captured image, most preferably areas including faces or facial regions (see also UK patent application number GB0031423.7 entitled "automatic cropping of electronic images", incorporated by reference). Regions of interest may be automatically or semi-automatically selected within an image in response to a selection signal (see, e.g., US published patent application 2003/0025812, incorporated by reference). Panning across an image may be performed preferably keeping a selected region such as a selected face or faces in view. An image processing system may be preferably employed with the panning method. A video camera system of another embodiment may implement tracking and/or zooming in relation to an object targeted by the camera (see, e.g., U.S. Pat. No. 5,812,193, incorporated by reference) For example, a user may teach the camera by presenting the camera with a view of an object, such that the camera may then seek to control a tracking motor so as to keep the object in view, and/or a zoom motor such that the size of the object with respect to the overall image remains fixed at the region learned by the camera. In a further embodiment, a model of a person's head may be provided such that the camera can correctly identify the head, or others like it, within it's field of view. Thus the device seeks to maintain a lock on a target. Such may be performed mechanistically or according to software and/or firmware provided within the camera. Advantageously, multiple targets such as multiple faces or facial regions may be tracked and/or zoomed, and preferably digitally enhanced, e.g., in view of aesthetic considerations.

Alternative Embodiments

Any of the following may be combined with the preferred embodiments, or may substitute for elements of preferred embodiments to provide alternative embodiments. A method of analyzing and processing a digital image using face detection within said image to achieve one or more desired image processing parameters is provided. Such parameters can be acquisition parameter, rendering parameters or a combination thereof. A group of pixels is identified that correspond to an image of a face within the digital image. Default values are determined of one or more parameters of at least some portion of said digital image. Values of the one or more parameters are adjusted within the digitally-detected image based upon an analysis of said digital image including said image of said face and said default values.

The digital image may be digitally-acquired and/or may be digitally-captured. Decisions for processing the digital image based on said face detection, selecting one or more parameters and/or for adjusting values of one or more parameters within the digital image may be automatically, semi-automatically or manually performed.

The one or more parameter may include orientation, color, tone, size, luminance, relative exposure, relative spatial location, tone reproduction, sharpness or focus or combinations thereof. The one or more parameters may include a mask that defines one or more regions where the one or more parameters are valid. The mask may include a continuous presentation of varying strength within different sub-regions of said one or more regions. The one or more parameters may include the same parameter differing in value based on said mask.

Two or more parameters may be concatenated into a single parameter. The digital image may be transformed based on values of the one or more parameters. An operation list may be created for the digital image based on values of the one or more parameters. The operation list may be embedded within the digital image or may be external to the digital image.

Values of orientation may be adjusted such that a rotation value for the digital image is determined. Values of the color, tone, size, luminance, relative exposure may be adjusted including manipulating a color, tonal, size, luminance, fill-flash balance of the digital image, respectively. Values of relative spatial location may be adjusted including adjusting a spatial location of an image of a face relative to at least one other region of the digital image. Values of focus may be adjusted including adjusting values of focus for enhancing a focus of the image of the face within the digital image.

One or more different degrees of simulated fill flash may be created by manual, semi-automatic or automatic adjustment. The analysis of the image of the face may include a comparison of an overall exposure to an exposure around the identified face. The exposure may be calculated based on a histogram. Digitally simulation of a fill flash may include optionally adjusting tone reproduction and/or locally adjusting sharpness. One or more objects estimated to be closer to the camera or of higher importance may be operated on in the simulated fill-flash. These objects determined to be closer to the camera or of higher importance may include one or more identified faces. A fill flash or an option for providing a suggested fill-flash may be automatically provided.

The method may be performed within a digital acquisition device, a digital rendering device, or an external device or a combination thereof. The face pixels may be identified, a false indication of another face within the image may be removed, and an indication of a face may be added within the image, each manually by a user, or semi-automatically or automatically using image processing apparatus. The face pixels identifying may be automatically performed by an image processing apparatus, and a manual verification of a correct detection of at least one face within the image may be provided.

A method of digital image processing using face detection to achieve a desired image parameter is further provided including identifying a group of pixels that correspond to an image of a face within a digitally-detected image. Initial values of one or more parameters of at least some of the pixels are determined. An initial parameter of the digitally-detected image is determined based on the initial values. Values of the one or more parameters of pixels within the digitally-detected image are automatically adjusted based upon a comparison of the initial parameter with the desired parameter or an option for adjusting the values is automatically provided.

The digitally-detected image may include a digitally-acquired and/or digitally-captured image. The initial parameter of the digitally-detected image may include an initial parameter of the face image. The one or more parameters may include any of orientation, color, tone, size, luminance, and focus. The method may be performed within a digital camera as part of a pre-acquisition stage, within a camera as part of post processing of the captured image or within external processing equipment. An option to manually remove a false indication of a face or to add an indication of a face within the image may be included. An option to manually override, the automated suggestion of the system, whether or not faces were detected, may be included.

The method may include identifying one or more sub-groups of pixels that correspond to one or more facial features of the face. Initial values of one or more parameters of pixels of the one or more sub-groups of pixels may be determined. An initial spatial parameter of the face within the digital image may be determined based on the initial values. The initial spatial parameter may include any of orientation, size and location.

When the spatial parameter is orientation, values of one or more parameters of pixels may be adjusted for re-orienting the image to an adjusted orientation. The one or more facial features may include one or more of an eye, a mouth, two eyes, a nose, an ear, and other facial features. Such features may also include the location of close-by skin which is associated with the neck and shoulders. The neck (and/or other features, see below) as an extension of the face, can be also used as an indicator to the orientation of the face and the body. The one or more facial features may include two or more features, and the initial orientation may be determined base on relative positions of the features that are determined based on the initial values. A shape such as a triangle may be generated for example between the two eyes and the center of the mouth, a golden rectangle as described above, or more generically, a polygon having points corresponding to preferably three or more features as vertices or axis.

Initial values of one or more chromatic parameters, such as color and tone, of pixels of the digital image may be determined. The values of one or more parameters may be automatically adjusted or an option to adjust the values to suggested values may be provided.

Many alternatives are possible for adjusting parameters of pixels corresponding to faces detected in a digital image based on the independent skin tone or luminance of each detected face. Other image correction techniques described herein may be adjusted based on skin tone or luminance. Other features or objects within a digital image may be separately adjusted based on luminance, color and/or tone. Techniques such as zooming, cropping, focusing, panning, orienting, and/or other techniques may be applied to faces or other features of objects within a digital image separately based on a specific luminance, color, tone and/or skin tone and/or ethnicity detected.

While an exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the claims that follow and their structural and functional equivalents.

In addition, in methods that may be performed according to the claims below and/or preferred embodiments herein, the operations have been described in selected typographical sequences. However, the sequences have been selected and so ordered for typographical convenience and are not intended to imply any particular order for performing the operations, unless a particular ordering is expressly provided or understood by those skilled in the art as being necessary.

All references cited herein, including patents, patent applications, published or unpublished, or articles or other publications or products, are hereby incorporated by reference. The background and summary of the invention are hereby incorporated by reference into the detailed description section as disclosing alternative embodiments and elements that may be substituted into preferred embodiments.

What is claimed is:

1. A method of processing a digital image using face detection to achieve one or more desired image processing parameters, comprising:
   identifying a group of pixels that correspond to a face image within the digital image;
   detecting a skin tone for the face image by determining one or more color or tonal values, or combinations thereof, for the group of pixels and comparing with one or more default color or tonal values, or combinations thereof; and
   adjusting values of one or more parameters for the group of pixels, including adjusting values of luminance to open up shadows within the face image by selectively applying fill-flash to regions within the face image in an amount based on the detected skin tone.

2. The method of claim 1, further comprising repeating the identifying, detecting and adjusting for a second face image having a different skin tone than the first face image, and the adjusting comprises applying fill-flash to the two face images in different relative amounts depending on the different skin tones.

3. The method of claim 2, wherein the adjusting comprises adjusting a luminance of each face image separately depending on the skin tone of each face image.

4. The method of claim 1, further comprising repeating the identifying, detecting and adjusting for a second face image having a different skin tone than the first face image, and the adjusting comprises adjusting luminance values of pixels of the two face images in different relative amounts depending on the different skin tones.

5. The method of claim 1, wherein the color or tonal values for the group of pixels comprise one or more average color or tonal values.

6. The method of claim 5, wherein the color or tonal values comprise multiple colors or tones, or combinations thereof, determined for each of multiple regions of the face image.

7. An image acquisition apparatus including an imaging optical system and digital image detector and storage medium, and having stored therein program instructions for programming one or more processors to perform a method of processing a digital image using face detection to achieve one or more desired image processing parameters, the method comprising:
   identifying a group of pixels that correspond to a face image within the digital image;
   detecting a skin tone for the face image by determining one or more color or tonal values, or combinations thereof, for the group of pixels and comparing with one or more default color or tonal values, or combinations thereof; and
   adjusting values of one or more parameters for the group of pixels, including adjusting values of luminance to open up shadows within the face image by selectively applying fill-flash to regions within the face image in an amount based on the detected skin tone.

8. The apparatus of claim 7, wherein the method further comprises repeating the identifying, detecting and adjusting for a second face image having a different skin tone than the first face image, and the adjusting comprises applying fill-flash to the two face images in different relative amounts depending on the different skin tones.

9. The apparatus of claim 8, wherein the adjusting comprises adjusting a luminance of each face image separately depending on the skin tone of each face image.

10. The apparatus of claim 7, wherein the method further comprises repeating the identifying, detecting and adjusting for a second face image having a different skin tone than the first face image, and the adjusting comprises adjusting luminance values of pixels of the two face images in different relative amounts depending on the different skin tones.

11. The apparatus of claim 7, wherein the color or tonal values for the group of pixels comprise one or more average color or tonal values.

12. The apparatus of claim 11, wherein the color or tonal values comprise multiple colors or tones, or combinations thereof, determined for each of multiple regions of the face image.

13. One or more digital storage devices having embodied therein program instructions for programming one or more processors to perform a method of processing a digital image using face detection to achieve one or more desired image processing parameters, the method comprising:
- identifying a group of pixels that correspond to a face image within the digital image;
- detecting a skin tone for the face image by determining one or more color or tonal values, or combinations thereof, for the group of pixels and comparing with one or more default color or tonal values, or combinations thereof; and
- adjusting values of one or more parameters for the group of pixels, including adjusting values of luminance to open up shadows within the face image by selectively applying fill-flash to regions within the face image in an amount based on the detected skin tone.

14. The one or more storage devices of claim 13, wherein the method further comprises repeating the identifying, detecting and adjusting for a second face image having a different skin tone than the first face image, and the adjusting comprises applying fill-flash to the two face images in different relative amounts depending on the different skin tones.

15. The one or more storage devices of claim 14, wherein the adjusting comprises adjusting a luminance of each face image separately depending on the skin tone of each face image.

16. The one or more storage devices of claim 13, wherein the method further comprises repeating the identifying, detecting and adjusting for a second face image having a different skin tone than the first face image, and the adjusting comprises adjusting luminance values of pixels of the two face images in different relative amounts depending on the different skin tones.

17. The one or more storage devices of claim 13, wherein the color or tonal values for the group of pixels comprise one or more average color or tonal values.

18. The one or more storage devices of claim 17, wherein the color or tonal values comprise multiple colors or tones, or combinations thereof, determined for each of multiple regions of the face image.

19. The method of claim 1, further comprising generating in-camera, capturing or otherwise obtaining in-camera a collection of low resolution images including said face image; and tracking said face image within said collection of low resolution images.

20. The apparatus of claim 7, wherein the method further comprises generating in-camera, capturing or otherwise obtaining in-camera a collection of low resolution images including said face image; and tracking said face image within said collection of low resolution images.

21. The one or more storage devices of claim 13, wherein the method further comprises generating in-camera, capturing or otherwise obtaining in-camera a collection of low resolution images including said face image; and tracking said face image within said collection of low resolution images.

* * * * *